US006949638B2

(12) United States Patent
Mittmann et al.

(10) Patent No.: US 6,949,638 B2
(45) Date of Patent: Sep. 27, 2005

(54) PHOTOLITHOGRAPHIC METHOD AND SYSTEM FOR EFFICIENT MASK USAGE IN MANUFACTURING DNA ARRAYS

(75) Inventors: Michael P. Mittmann, Palo Alto, CA (US); Earl A. Hubbell, Los Angeles, CA (US)

(73) Assignee: Affymetrix, Inc., Santa Clara, CA (US)

( * ) Notice: Subject to any disclaimer, the term of this patent is extended or adjusted under 35 U.S.C. 154(b) by 455 days.

(21) Appl. No.: 09/824,931

(22) Filed: Apr. 3, 2001

(65) Prior Publication Data

US 2002/0102564 A1 Aug. 1, 2002

Related U.S. Application Data

(60) Provisional application No. 60/265,103, filed on Jan. 29, 2001.

(51) Int. Cl.[7] ................... C07H 21/00; C07H 17/00; C12Q 1/68; G01N 33/52
(52) U.S. Cl. ................ 536/25.3; 530/333; 435/6; 435/7.1
(58) Field of Search ................ 536/25.3; 530/333; 435/6, 7.1

(56) References Cited

U.S. PATENT DOCUMENTS

| | | | |
|---|---|---|---|
| 5,571,639 A | 11/1996 | Hubbell et al. | |
| 5,593,839 A | 1/1997 | Hubbell et al. | |
| 5,856,101 A | 1/1999 | Hubbell et al. | |
| 6,153,743 A | 11/2000 | Hubbell et al. | |
| 6,185,561 B1 | 2/2001 | Balaban et al. | |
| 6,188,783 B1 | 2/2001 | Balaban et al. | |
| 2002/0094533 A1 * | 7/2002 | Hess et al. | 435/6 |

FOREIGN PATENT DOCUMENTS

| | | |
|---|---|---|
| EP | 0 374 701 | 6/1990 |
| WO | WO 97/31256 | 8/1997 |
| WO | WO 99/32663 | 7/1999 |

OTHER PUBLICATIONS

U.S. Appl. No. 60/239,538.*

* cited by examiner

Primary Examiner—Ardin H. Marschel
(74) Attorney, Agent, or Firm—William R. McCarthy, III; Philip L. McGarrigle; Alan B. Sherr

(57) ABSTRACT

Systems, methods, and products are described for synthesizing probe arrays of polymers. A mask is used that includes reticle areas, each of which includes a number of reticles associated with a same synthesis area on a substrate. A method includes (a) aligning the mask with respect to the substrate so that a first reticle of a first reticle area is aligned with a first synthesis area and so that a second reticle of the first reticle area is aligned with a first discard area on the substrate; (b) coupling monomers on the first synthesis area at locations determined by the first reticle; (c) re-aligning the mask with respect to the substrate so that the second reticle is aligned with the first synthesis area; and (d) coupling monomers on the first synthesis area at locations determined by the second reticle. The monomers may be, for example, nucleotides, amino acids or saccharides.

18 Claims, 14 Drawing Sheets

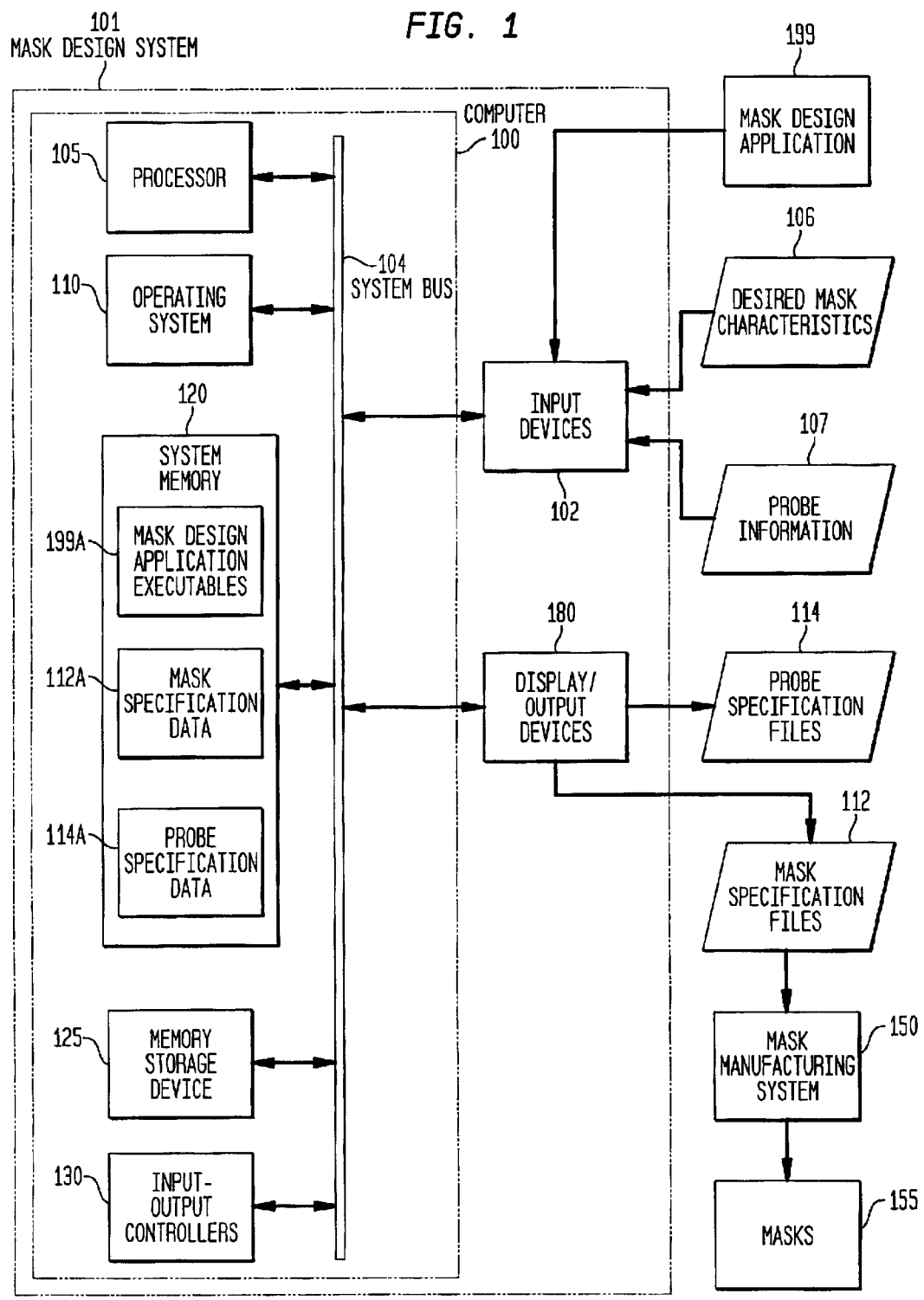

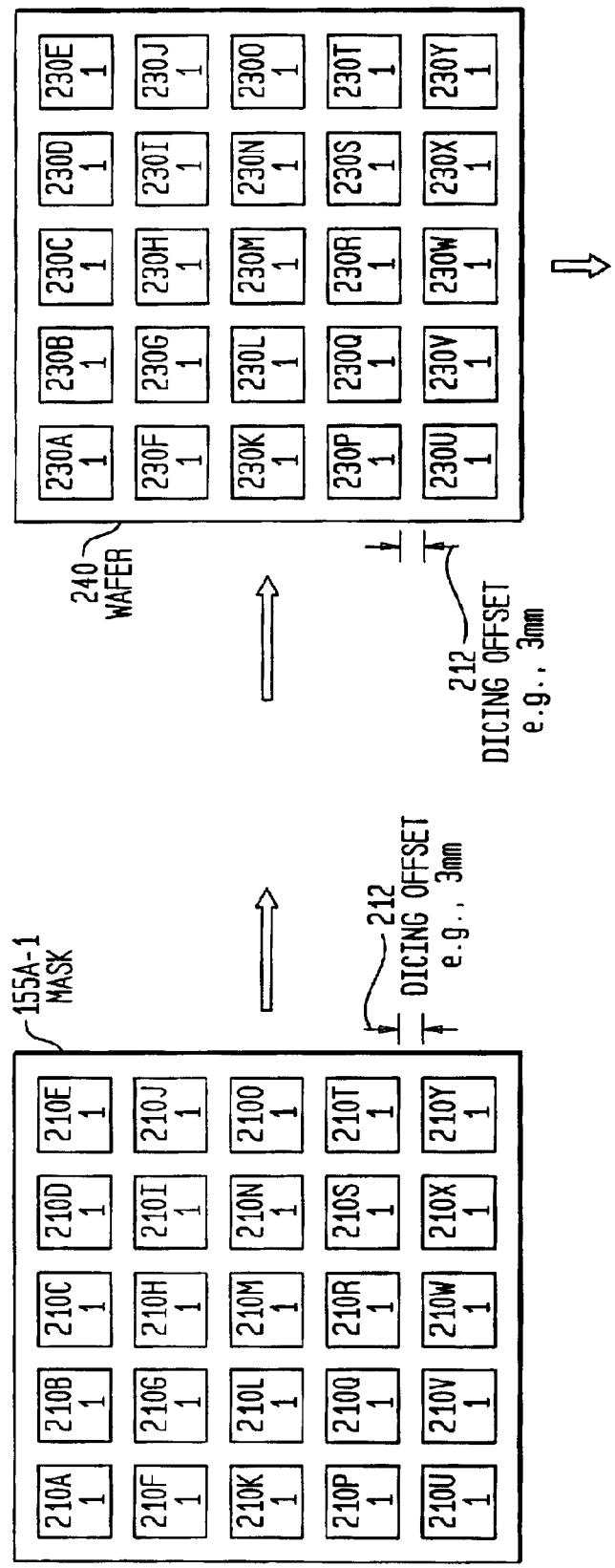

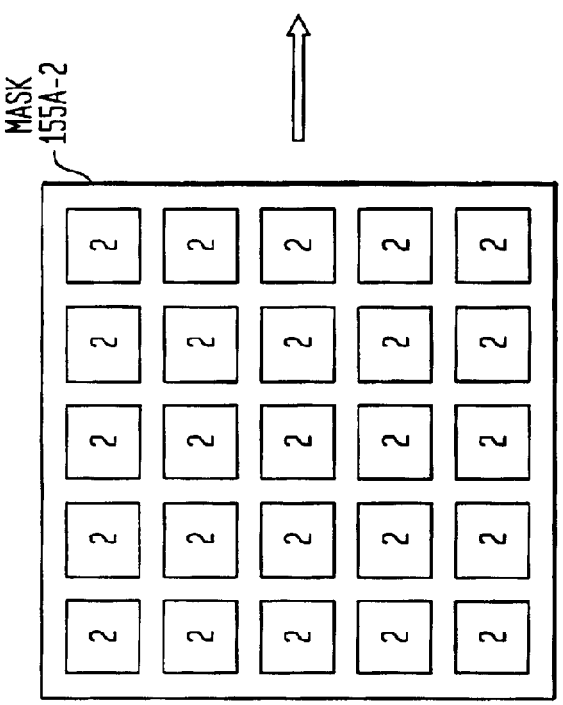
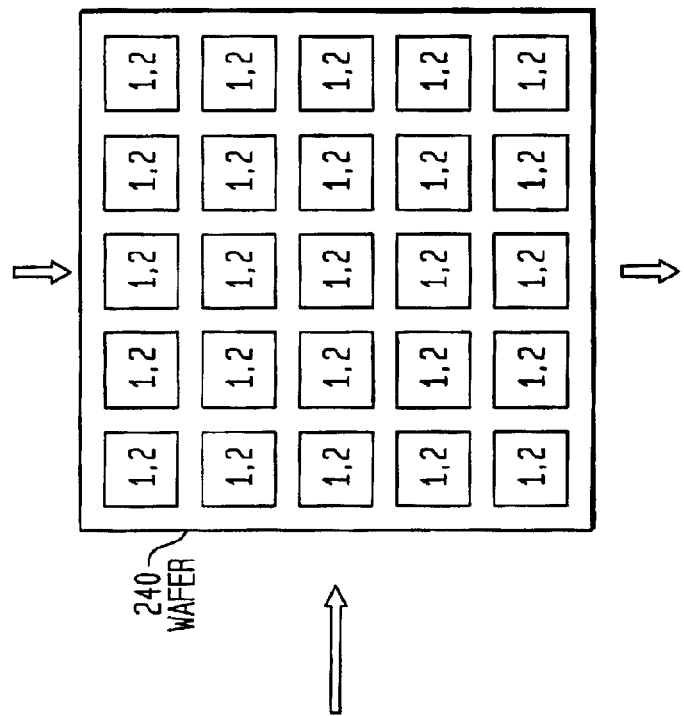

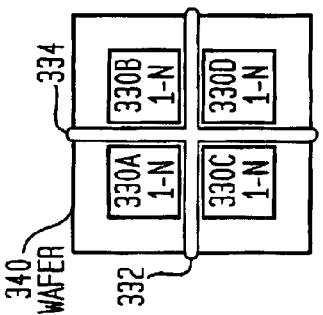
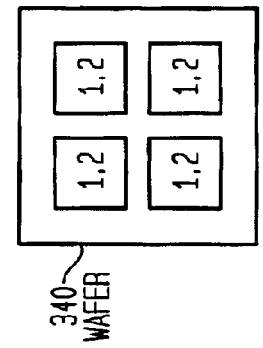
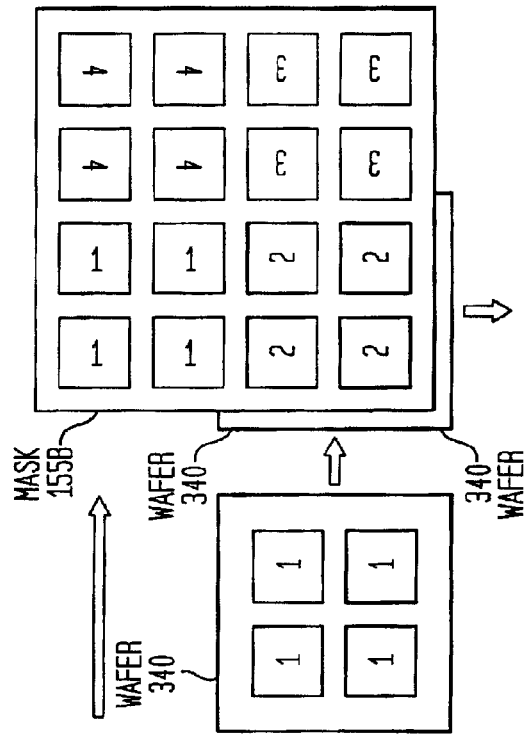
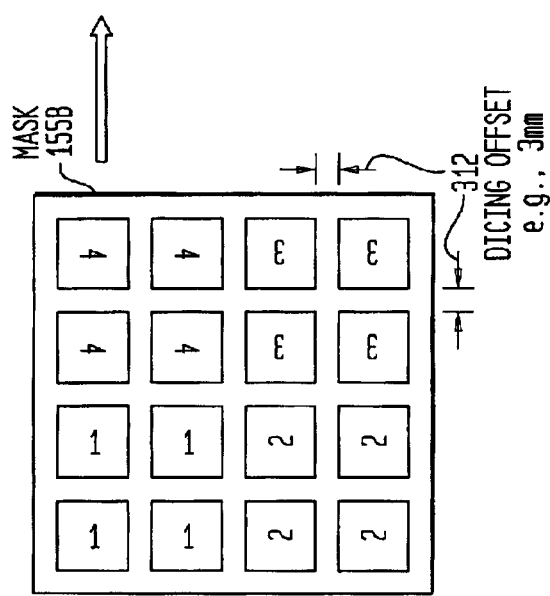

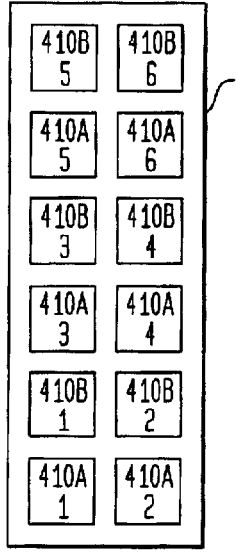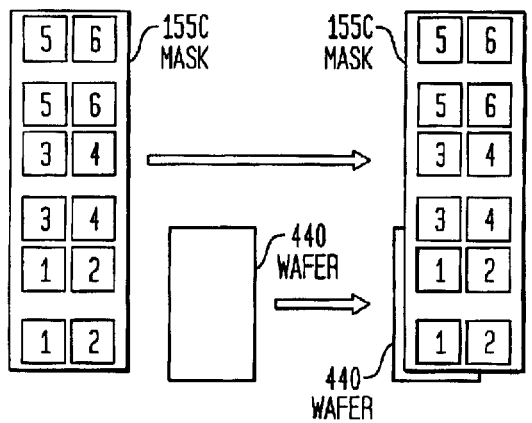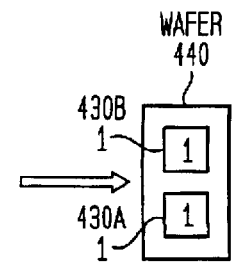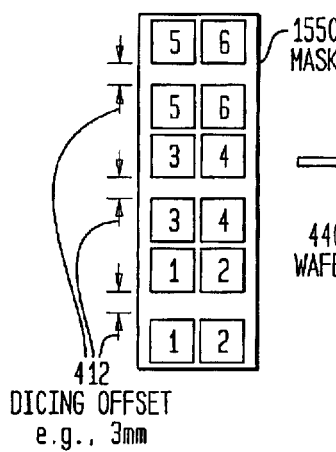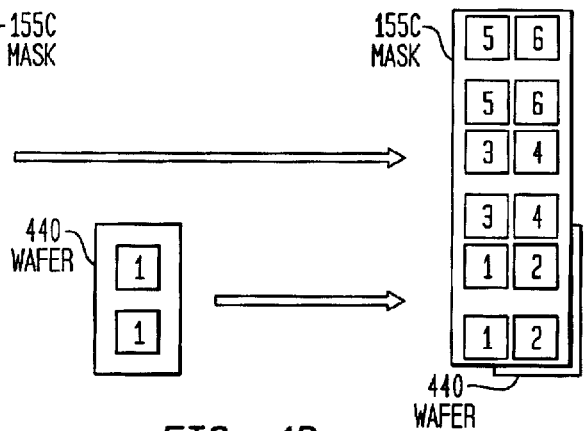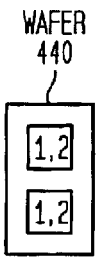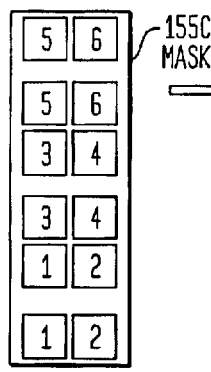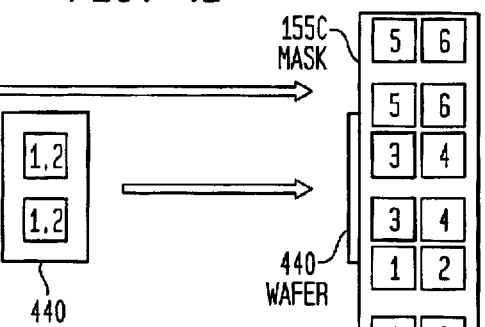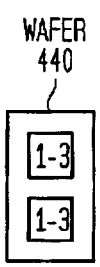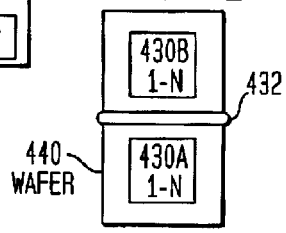

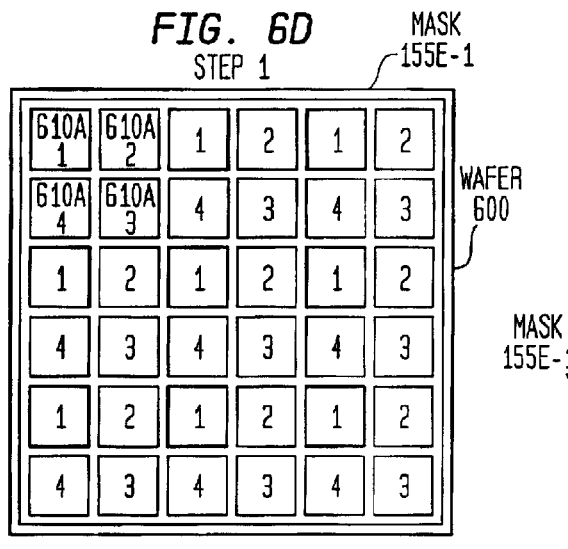
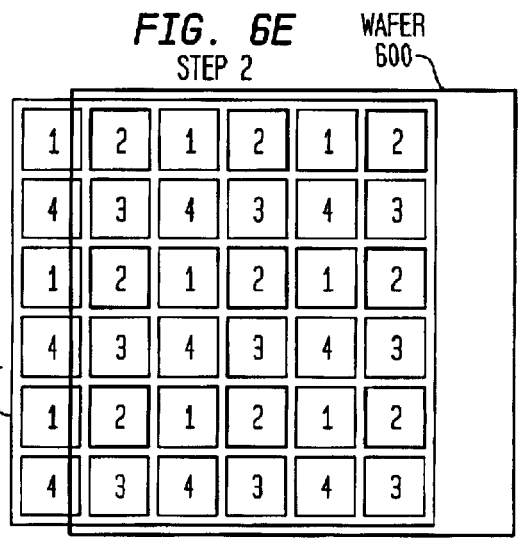
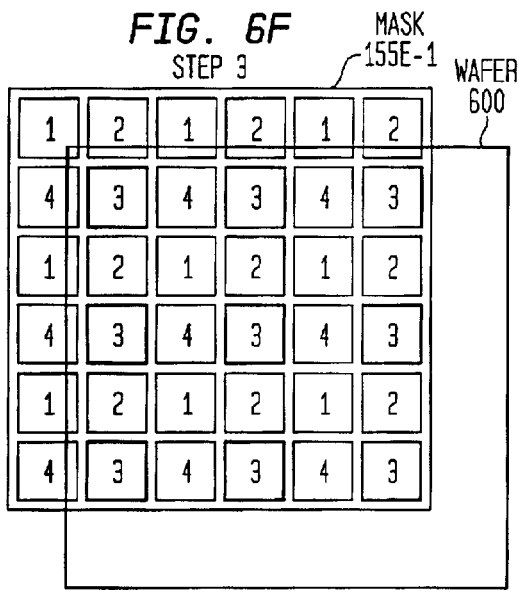
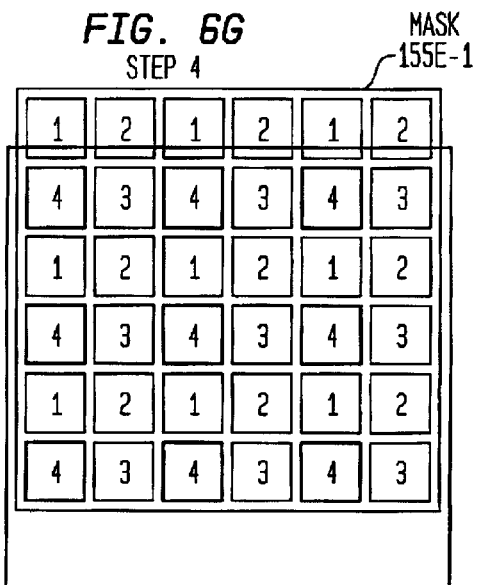
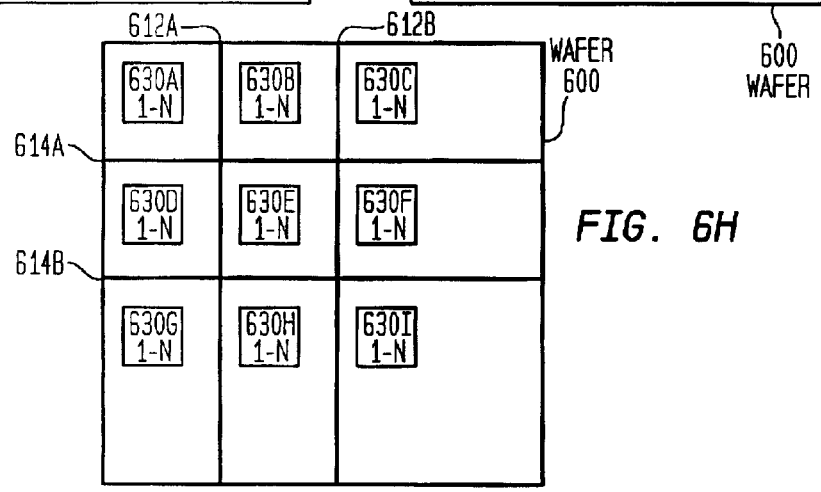

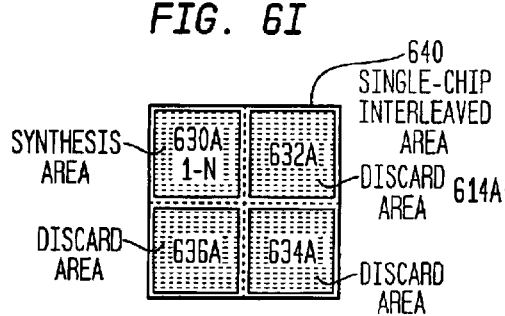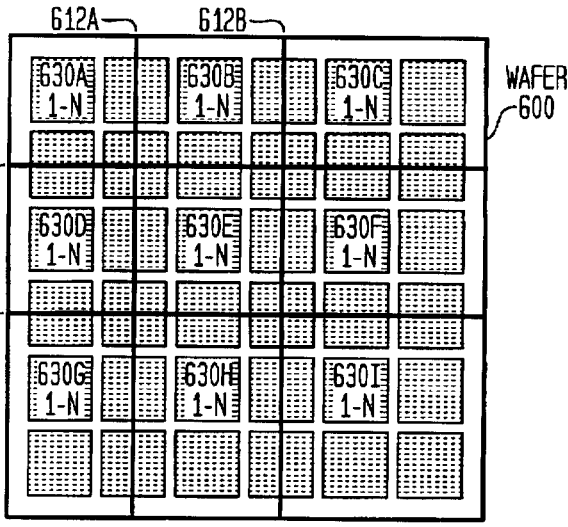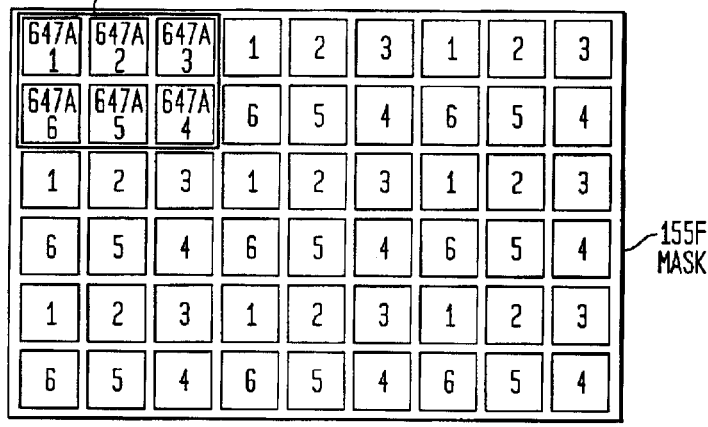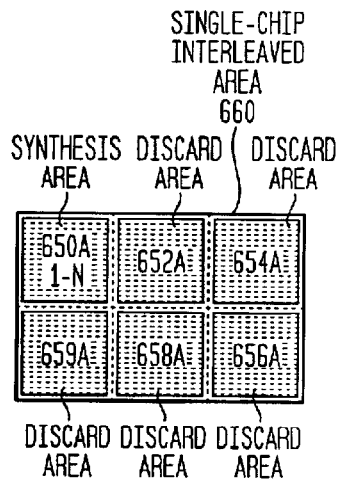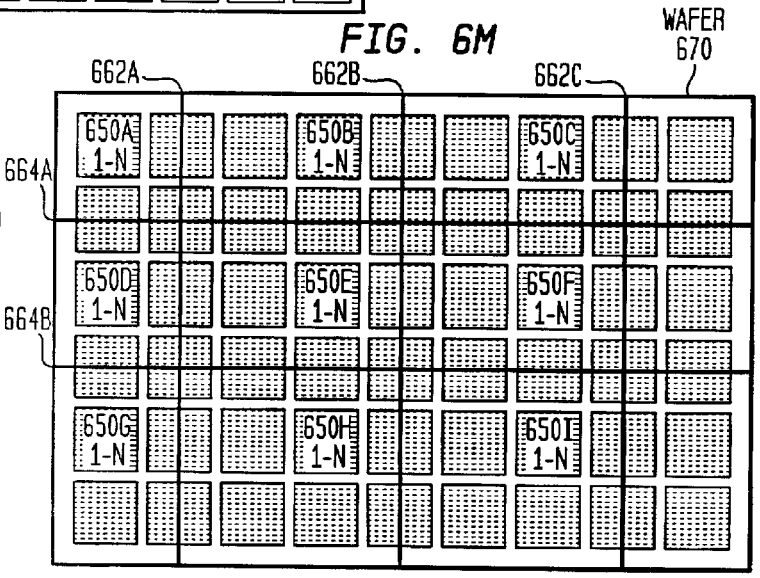

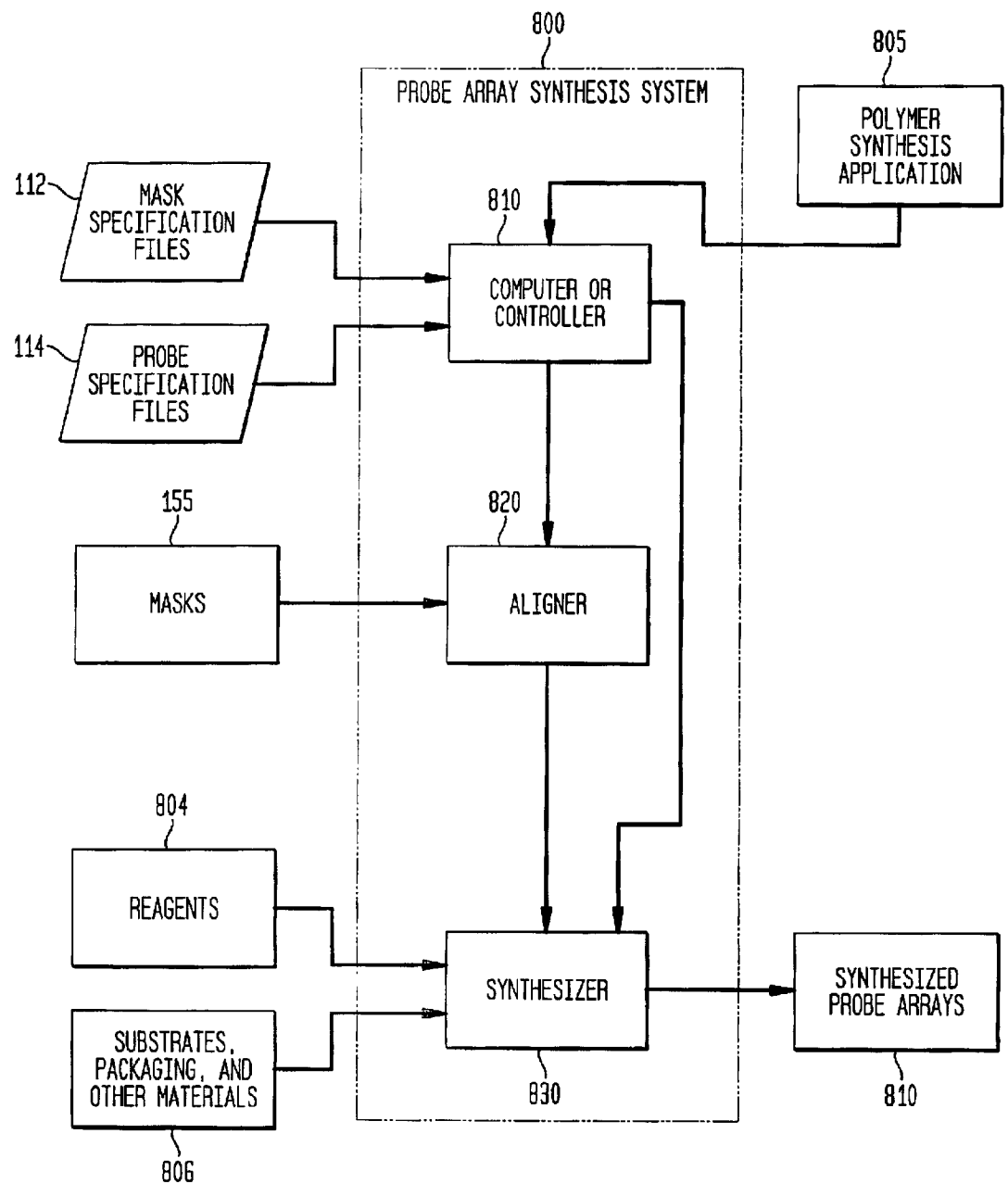

PHOTOLITHOGRAPHIC METHOD AND SYSTEM FOR EFFICIENT MASK USAGE IN MANUFACTURING DNA ARRAYS

RELATED APPLICATIONS

The present application claims priority from U.S. Provisional Patent Application Ser. No. 60/265,103, entitled "RAPID FLEXIBLE CONTENT ARRAY AND ONLINE ORDERING SYSTEM," filed Jan. 29, 2001, hereby incorporated herein by reference in its entirety for all purposes.

FIELD OF THE INVENTION

The present invention is related to systems, methods, and products providing lithographic masks used to form high-density probes of biological materials on a substrate.

BACKGROUND

U.S. Pat. No. 5,424,186 to Fodor, et al., describes a technique for, among other things, forming and using high density arrays of probes comprising molecules such as oligonucleotide, RNA, peptides, polysaccharides, and other materials. Arrays of oligonucleotides or peptides, for example, are formed on the surface by sequentially removing a photo-removable group from a surface, coupling a monomer to the exposed region of the surface, and repeating the process. Nucleic acid probe arrays synthesized in this manner, such as Affymetrix® GeneChip® probe arrays from Affymetrix, Inc. of Santa Clara, Calif., have been used to generate unprecedented amounts of information about biological systems. Analysis of these data may lead to the development of new drugs and new diagnostic tools.

A typical step in the process of synthesizing these probe arrays is to design a mask that will define the locations on a substrate that are exposed to light. Some systems and methods useful in the design and/or use of such masks are described in the following U.S. Pat. No. 5,571,639 to Hubbell, et al.; U.S. Pat. No. 5,593,839 to Hubbell, et al.; U.S. Pat. No. 5,856,101 to Hubbell, et al.; U.S. Pat. No. 6,153,743 to Hubbell, et al.; and U.S. Pat. No. 6,188,783 to Balaban, et al., each of which is hereby incorporated herein by reference for all purposes. Notwithstanding the advances described in these patents, it is desirable to identify additional techniques for designing and using masks in the manufacture of probe arrays.

SUMMARY OF THE INVENTION

Systems, methods, computer program products, masks, and probe arrays produced thereby, are described with reference to illustrative, non-limiting, embodiments. For example, while certain systems, methods, computer software products, masks, and probe arrays are described with respect to the manufacture and/or use of Affymetrix® GeneChip® probe arrays, these descriptions are merely illustrative. Other implementations are possible, for example, with respect to other types of probe arrays. Moreover, possible implementations are not limited to probe arrays. That is, the synthesized polymers need not be used as probes but may be employed with respect to any of a variety of conventional combinatorial chemistry purposes and uses.

In accordance with some embodiments, a method is described for synthesizing polymers on a substrate using one or more masks. In some implementations, the polymers synthesized on the substrate comprise probes in a probe array. The masks each include reticle areas made up of reticles. A reticle is made up of areas transparent to the photolithographic radiation (hereafter, simply referred to for convenience as "light"), and also is made up of occluded areas through which the light does not pass. The transparent areas are sometimes referred to as "flashes." Each of the reticles in a particular reticle area is associated with the same synthesis area on the substrate. In those implementations in which the combinatorial chemistry is directed to producing probe arrays, the term "synthesis area" is used herein to refer to an area of the substrate on which probes are synthesized that are intended to be included in the synthesized probe arrays. In these implementations, a probe of a probe array generally may be a polymer having a sequence such that the probe is capable of hybridizing with potential targets, or having a sequence serving as a control to assess the hybridization process. In contrast, the term "discard area" is used herein to refer to an area on the substrate through which dicing lines may be cut to physically separate the substrate into two or more probe arrays. A part or all of a discard area may contain synthesized polymers that are not intended for use as probes (or, in implementations other than probe arrays, are not intended for the purpose of the combinatorial chemistry). That is, in the illustrated implementations, although polymers may be synthesized in discard areas, these polymers may be discarded or otherwise ignored or destroyed rather than used as probes in a synthesized probe array. The polymers in discard areas may have sequences suitable for hybridization or control, but need not. In some implementations, the term "discard area" may be used more broadly to also include areas not used for cutting but used for joining the substrate to packaging, or for other purposes not including the purpose of providing a synthesis area.

The method includes the following steps: (a) for each reticle area, sequentially aligning two or more of the reticles of that reticle area with the associated synthesis area; and (b) for each sequential alignment, coupling monomers on the substrate at locations determined by the aligned reticles. The monomers of this method, and of other embodiments and implementations described herein, may include nucleotides, amino acids, or saccharides, for example.

In accordance with this method, the reticle areas are substantially contiguously arranged on the mask, and the plurality of reticles within each of the reticle areas are substantially contiguously arranged within the reticle area. The term "substantially contiguously" is used in this context to mean that reticles in a reticle area may abut each other, and that reticle areas may abut each other. That is, there generally need not be any spaces between the reticles or between the reticle areas. However, the term "substantially contiguously" is used broadly herein to include implementations, such as that illustrated in the detailed description below, in which narrow boundary areas are provided between reticles and/or between reticle areas. As described in greater detail below, these narrow boundary areas may be provided for a variety of practical reasons related to making masks, scanning labeled probe-target pairs, and other reasons. Notably, however, they are not provided for the reason of reserving, by themselves, a space on the substrate for dicing.

In some implementations of the method, each reticle area may be made up of reticles arranged in a particular pattern that is the same for all reticle areas. For example, the pattern may be an array of rows and columns in which the rows have a height H (which is the height of the reticles, plus a boundary area, if any) and the columns may have a width W (which is the width of the reticles, plus a boundary area, if any). In some aspects of these implementations, the sequential alignment of step (a) may include translating the mask with respect to the substrate by a sequence of steps. The translation distance at each step is determined by the height H or the width W. For example, a step may consist of a translation W to the right or, as another example, a translation W to the right and a translation H down. The translation between the mask and substrate is relative, and may thus be accomplished by moving the mask and keeping the substrate immobile, by moving the substrate and keeping the mask immobile, or by moving both to varying degrees.

In some implementations of the method, step (b) may include coupling a same monomer for each of the aligned reticles. Step (b) may also include directing light through the aligned reticles to de-protect the locations for coupling.

Other embodiments described herein are directed to systems for synthesizing polymers on a substrate. In one implementation, the system includes a mask having a plurality of reticle areas, wherein each reticle area includes two or more reticles, each of which is associated with a same synthesis area on the substrate. The system also has an aligner that, for each reticle area, sequentially aligns two or more of the reticles of that reticle area with the associated synthesis area. Another element of the system is a synthesizer that, for each sequential alignment, causes monomers to be coupled on the substrate at locations determined by the aligned reticles. In these implementations, the reticle areas are substantially contiguously arranged on the mask, and the reticles within each of the reticle areas are substantially contiguously arranged within the reticle area.

Further embodiments are directed to a mask for synthesizing polymers on a substrate. The mask has substantially contiguously arranged reticle areas and, within each reticle area, substantially contiguous reticles. Each of the reticles in a same reticle area is associated with a same synthesis area on the substrate and is constructed and arranged for synthesizing polymers by enabling the coupling of monomers on the same synthesis area at locations determined by the reticles.

Yet other embodiments are directed to a method for manufacturing a mask for synthesizing polymers on a substrate. The method includes the step of identifying two or more reticle areas substantially contiguously arranged on the mask. Another step is to construct and arrange two or more substantially contiguous reticles within each reticle area, each of which is associated with a same synthesis area on the substrate. The reticles further are constructed and arranged for synthesizing polymers by enabling the coupling of monomers on the same synthesis area at locations determined by the reticles of a particular reticle area.

Also described herein is a probe array including polymers synthesized on a substrate by a method that includes the steps of: (a) providing at least one mask having two or more reticle areas, wherein each reticle area comprises two or more reticles, each of which is associated with a same synthesis area on the substrate; (b) for each reticle area, sequentially aligning two or more of the plurality of reticles of that reticle area with the associated synthesis area; and (c) for each sequential alignment, coupling monomers on the substrate at locations determined by the aligned reticles. The two or more reticle areas are substantially contiguously arranged on the mask, and the two or more reticles within each of the reticle areas are substantially contiguously arranged within the reticle area.

In other embodiments, a computer program product is described for synthesizing polymers on a substrate using a mask having a plurality of reticle areas, wherein each reticle area comprises two or more reticles, each of which is associated with a same synthesis area on the substrate. The product includes a computer usable medium storing control logic that, when executed on a computer system, performs a method including the steps of: (a) for each reticle area, sequentially aligning two or more of the reticles of that reticle area with the associated synthesis area; and (b) for each sequential alignment, coupling monomers on the substrate at locations determined by the aligned reticles. The reticle areas are substantially contiguously arranged on the mask, and the reticles within each of the reticle areas are substantially contiguously arranged within the reticle area.

Also described herein is a method for synthesizing probe arrays of polymers on a substrate using a mask having two or more reticle areas, wherein each reticle area includes two or more reticles, each of which is associated with a same synthesis area on the substrate. The method includes the following steps: (a) aligning the mask with respect to the substrate so that a first reticle of a first reticle area is aligned with a first synthesis area associated with the two or more reticles of the first reticle area, and so that a second reticle of the first reticle area is aligned with a first discard area on the substrate; (b) coupling monomers on the first synthesis area at locations determined by the first reticle; (c) re-aligning the mask with respect to the substrate so that the second reticle is aligned with the first synthesis area; and (d) coupling monomers on the first synthesis area at locations determined by the second reticle.

In general, the preceding steps may be repeated so that each of the reticles of a reticle area is aligned during a synthesis step with the synthesis area associated with that reticle area. When a reticle is aligned with the synthesis area, the other reticles of the same reticle area typically are not aligned with that, or another, synthesis area. Rather, they typically are aligned with a discard area. A further step in some implementations of the method is to dice the substrate. The dicing is done at least partially within the first discard area. Typically, the dicing physically separates a probe array, including the first synthesis area on the substrate, from at least one other synthesis area on the substrate.

A further embodiment described herein consists of a system for synthesizing probe arrays of polymers on a substrate. The system includes a mask having two or more reticle areas, wherein each reticle area comprises a plurality of reticles, each of which is associated with a same synthesis area on the substrate. Also included in the system is an aligner that (i) aligns the mask with respect to the substrate so that a first reticle of a first reticle area is aligned with a first synthesis area associated with the plurality of reticles of the first reticle area, and so that a second reticle of the first reticle area is aligned with a first discard area on the substrate, and (ii) re-aligns the mask with respect to the substrate so that the second reticle is aligned with the first synthesis area. Another element of the system is a synthesizer that (i) couples monomers on the first synthesis area at locations determined by the first reticle when the first reticle is aligned with the first synthesis area, and (ii) couples monomers on the first synthesis area at locations determined by the second reticle when the second reticle is aligned with the first synthesis area. Typically, the synthesizer further is constructed and arranged to direct light through the aligned reticles to de-protect the locations for coupling.

Yet another embodiment consists of a probe array comprising polymers synthesized on a substrate by a method that includes the following steps: (a) providing at least one mask having a plurality of reticle areas, wherein each reticle area comprises a plurality of reticles, each of which is associated with a same synthesis area on the substrate; (b) aligning the mask with respect to the substrate so that a first reticle of a first reticle area is aligned with a first synthesis area associated with the plurality of reticles of the first reticle area, and so that a second reticle of the first reticle area is aligned with a first discard area on the substrate; (c) coupling monomers on the first synthesis area at locations determined by the first reticle; (d) re-aligning the mask with respect to the substrate so that the second reticle is aligned with the first synthesis area; and (e) coupling monomers on the first synthesis area at locations determined by the second reticle. A further embodiment is a computer program product for synthesizing polymers on a substrate using a mask having a plurality of reticle areas. Each reticle area includes a plurality of reticles, each of which is associated with a same synthesis area on the substrate. The product includes a computer usable medium storing control logic that, when executed on a computer system, performs a method including: (a) aligning the mask with respect to the substrate so that a first reticle of a first reticle area is aligned with a first synthesis area associated with the plurality of reticles of the first reticle area, and so that a second reticle of the first reticle area is aligned with a first discard area on the substrate; (b) coupling monomers on the first synthesis area at locations determined by the first reticle; (c) re-aligning the mask with respect to the substrate so that the second reticle is aligned with the first synthesis area; and (d) coupling monomers on the first synthesis area at locations determined by the second reticle.

The preceding embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to others. Also, any one or more function, step, operation, or technique described elsewhere in this specification may, in alternative embodiments or implementations, be combined with any one or more function, step, operation, or technique described in the summary. Thus, the above embodiments and implementations are illustrative rather than limiting.

BRIEF DESCRIPTION OF THE DRAWINGS

The above and other embodiments and implementations will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 120 appears first in FIG. 1).

FIG. 1 is a functional block diagram of one embodiment of a system for designing and manufacturing masks;

FIGS. 2C through 2H are simplified graphical representations of a conventional method for synthesizing probes on a substrate, and then dicing the substrate to provide probe arrays, using one or more masks of the conventional type shown in FIG. 2B;

FIGS. 3A through 3F are simplified graphical representations of a method for synthesizing probes on a substrate, and then dicing the substrate to provide probe arrays, using one or more masks, each of which has reticles used in separate synthesis steps;

FIGS. 4A through 4E are simplified graphical representations of another method for synthesizing probes on a substrate, and then dicing the substrate to provide probe arrays, using one or more masks, each of which has reticles used in separate synthesis steps;

FIGS. 6D through 6H are simplified graphical representations of one embodiment of a method for synthesizing probes on a substrate, and then dicing the substrate to provide probe arrays, using one or more masks such as those of FIGS. 6A through 6C;

FIGS. 6I and 6J are simplified graphical representations showing aspects of the substrate of FIGS. 6E through 6H in greater detail;

FIG. 6K is a simplified graphical representation of yet another embodiment of a mask having substantially contiguous reticles and reticle areas, and FIGS. 6L and 6M are simplified graphical representations of another implementation of the method for synthesizing probes on a substrate, and then dicing the substrate to provide probe arrays, using the mask of FIG. 6K;

FIG. 8 is a functional block diagram of one embodiment of a probe array synthesis system suitable for making probe arrays using masks having substantially contiguous reticles and reticle areas.

DETAILED DESCRIPTION

Figure 2A:
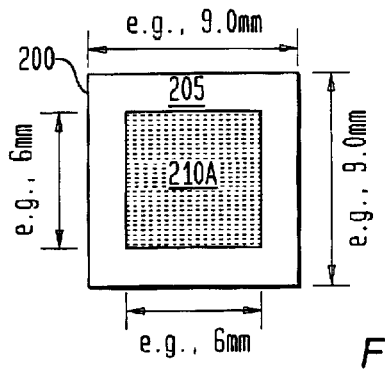
FIGS. 2A and 2B are simplified graphical representations of a representative reticle and a mask in accordance with a conventional arrangement of reticles on a mask.

Detailed descriptions are now provided with respect to systems, methods, software program products, masks produced thereby, probe arrays produced thereby, and combinations thereof.

Synthesized Probe Arrays

Various techniques and technologies may be used for synthesizing dense arrays of biological materials on or in a substrate or support. For example, Affymetrix® GeneChip(®) arrays are synthesized in accordance with techniques sometimes referred to as VLSIPS™ (Very Large Scale Immobilized Polymer Synthesis) technologies. Some aspects of VLSIPS™ technologies are described in the following U.S. Pat. No. 5,424,186 to Fodor, et al.; U.S. Pat. No. 5,143,854 to Pirrung, et al.; U.S. Pat. No. 5,445,934 to Fodor, et al; U.S. Pat. No. 5,744,305 to Fodor, et al.; U.S. Pat. No. 5,831,070 to Pease, et al.; U.S. Pat. No. 5,837,832 to Chee, et al.; U.S. Pat. No. 6,022,963 to McGall, et al.; and U.S. Pat. No. 6,083,697 to Beech et al. Each of these patents is hereby incorporated by reference in its entirety. The probes of these arrays in some implementations consist of oligonucleotides, which are synthesized by methods that include the steps of activating regions of a substrate and then contacting the substrate with a selected monomer solution. The regions are activated with a light source shown through a mask in a manner similar to photolithography techniques used in the fabrication of integrated circuits. Other regions of the substrate remain inactive because the mask blocks them from illumination. By repeatedly activating different sets of regions and contacting different monomer solutions with the substrate, a diverse array of polymers is produced on the substrate. Various other steps, such as washing unreacted monomer solution from the substrate, are employed in various implementations of these methods.

Additional techniques for synthesizing and using high-density probe arrays are described in U.S. Pat. No. 5,384,261 to Winkler, et al. These techniques include systems for mechanically protecting portions of a substrate and selectively de-protecting and coupling materials to the substrate using light-directed methods. Still further techniques for probe array synthesis are provided in U.S. Pat. No. 6,121,048 to Zaffaroni, et al. The '261 and '048 patents also are incorporated herein by reference for all purposes.

The probes of these synthesized probe arrays typically are used in conjunction with tagged biological samples such as cells, proteins, genes or EST's, other DNA sequences, or other biological elements. These samples, referred to herein as "targets," are processed so that, typically, they are spatially associated with certain probes in the probe array. For example, one or more chemically tagged biological samples, i.e., the targets, are distributed over the probe array. Some targets hybridize with at least partially complementary probes and remain at the probe locations, while non-hybridized targets are washed away. These hybridized targets, with their "tags" or "labels," are thus spatially associated with the targets' complementary probes. The hybridized probe and target may sometimes be referred to as a "probe-target pair." Detection of these pairs can serve a variety of purposes, such as to determine whether a target nucleic acid has a nucleotide sequence identical to or different from a specific reference sequence. See, for example, U.S. Pat. No. 5,837,832, referred to and incorporated above. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The '992, '138, and '092 patents, and publication WO99/05323, are incorporated by reference herein in their entireties for all purposes.

Probes typically are able to detect the expression of corresponding genes or EST's by detecting the presence or abundance of mRNA transcripts present in the target. This detection may, in turn, be accomplished by detecting labeled cRNA that is derived from cDNA derived from the mRNA in the target. In general, a group of probes, sometimes referred to as a probe set, contains sub-sequences in unique regions of the transcripts and does not correspond to a full gene sequence. Further details regarding the design and use of probes are provided in U.S. Pat. No. 6,188,783, incorporated above, and in PCT Application Ser. No. PCT/US 01/02316, filed Jan. 24, 2001, and hereby incorporated herein in its entirety for all purposes.

Labeled targets in hybridized probe arrays may be detected using various commercial devices, sometimes referred to as "scanners." Scanners image the targets by detecting fluorescent or other emissions from the labels, or by detecting transmitted, reflected, or scattered radiation. A typical scheme employs optical and other elements to provide excitation light and to selectively collect the emissions. Also generally included are various light-detector systems employing photodiodes, charge-coupled devices, photomultiplier tubes, or similar devices to register the collected emissions. For example, a scanning system for use with a fluorescent label is described in U.S. Pat. No. 5,143,854, incorporated by reference above. Other scanners or scanning systems are described in U.S. Pat. Nos. 5,578,832; 5,631,734; 5,834,758; 5,936,324; 5,981,956; 6,025,601; 6,141,096; 6,185,030; and 6,201,639, and in PCT Application PCT/US99/06097 (published as WO99/47964), each of which is hereby incorporated by reference in its entirety for all purposes.

Mask Design System 101 and Mask Manufacturing System 150

FIG. 1 includes a functional block diagram of an illustrative mask design system 101 for designing the masks used to produce synthesized probe arrays. In particular, system 101 provides data, represented as mask specification files 112, that may be used by mask manufacturing system 150 to produce masks 155. Probe information 107 is provided to system 101. Information 107 specifies the desired sequences of polymers constituting probes derived and presented in accordance with known techniques and systems such as described, for example, in U.S. Pat. No. 5,571,639, incorporated by reference above. Desired mask characteristics 106 also are provided to system 101. Characteristics 106 may include, for example, specification of substantially contiguous reticles in substantially contiguous reticle areas, as described in greater detail below with respect to the illustrative masks of FIGS. 5AC, 6A–C, 6K, and with respects to aspects of the method steps represented in FIG. 7. Illustrative mask design application 199 is any of a variety of conventional software applications, such as a computer-aided design application, that may be used to generate mask specification files 112 based, at least in part, on desired mask characteristics 106 and probe information 107. Aspects of computer-aided design systems are described in U.S. Pat. Nos. 5,593,839 and 5,856,101, both of which have been incorporated herein. Application 199 typically is loaded via an input device 102 (such as a floppy disk or CD-ROM reader) into a memory device (e.g., RAM or hard drive) of computer 100 for execution, as represented by mask design application executables 199A. Computer 100 may be any type of computer platform such as a workstation, a personal computer, a server, or any other present or future computer. Computer 100 typically includes known components such as a processor 105, an operating system 110, a system memory 120, memory storage devices 125, and input-output controllers 130, all of which typically communicate in accordance with known techniques such as via system bus 104.

As will be appreciated by those of ordinary skill in the relevant art, mask specification files 112 include data specifying a layout of reticles on one or more masks consistent with desired mask characteristics 106 and probe information 107. As also will be appreciated by those of ordinary skill in the relevant art, probe specification files 114 include information specifying the order in which monomers may be applied in a probe array synthesizer that synthesizes probe arrays using masks 155. Although the word "files" is used for convenience of illustration with respect to files 112 and 114, the word is used broadly to include any type of data structure or technique for storing or transmitting data in any form or format.

Mask manufacturing system 150 may be any of a variety of conventional systems for producing masks, or a mask-producing system of a type that may be developed in the future. Masks 155 produced by system 150 typically comprise lithographic members such as chrome on glass, as one illustrative and non-limiting example. Reticles on the mask selectively direct light to a substrate during an exposure in accordance with known techniques. As noted above with respect to an illustrative example, the light may activate linker molecules at sites on the substrate determined by openings in the reticles through which the light passes. Mask manufacturing system 150 is capable of producing masks 155 of conventional design or of an improved design in accordance with aspects of the present invention, depending on whether desired mask characteristics 106 are conventional or otherwise.

Figure 2B:
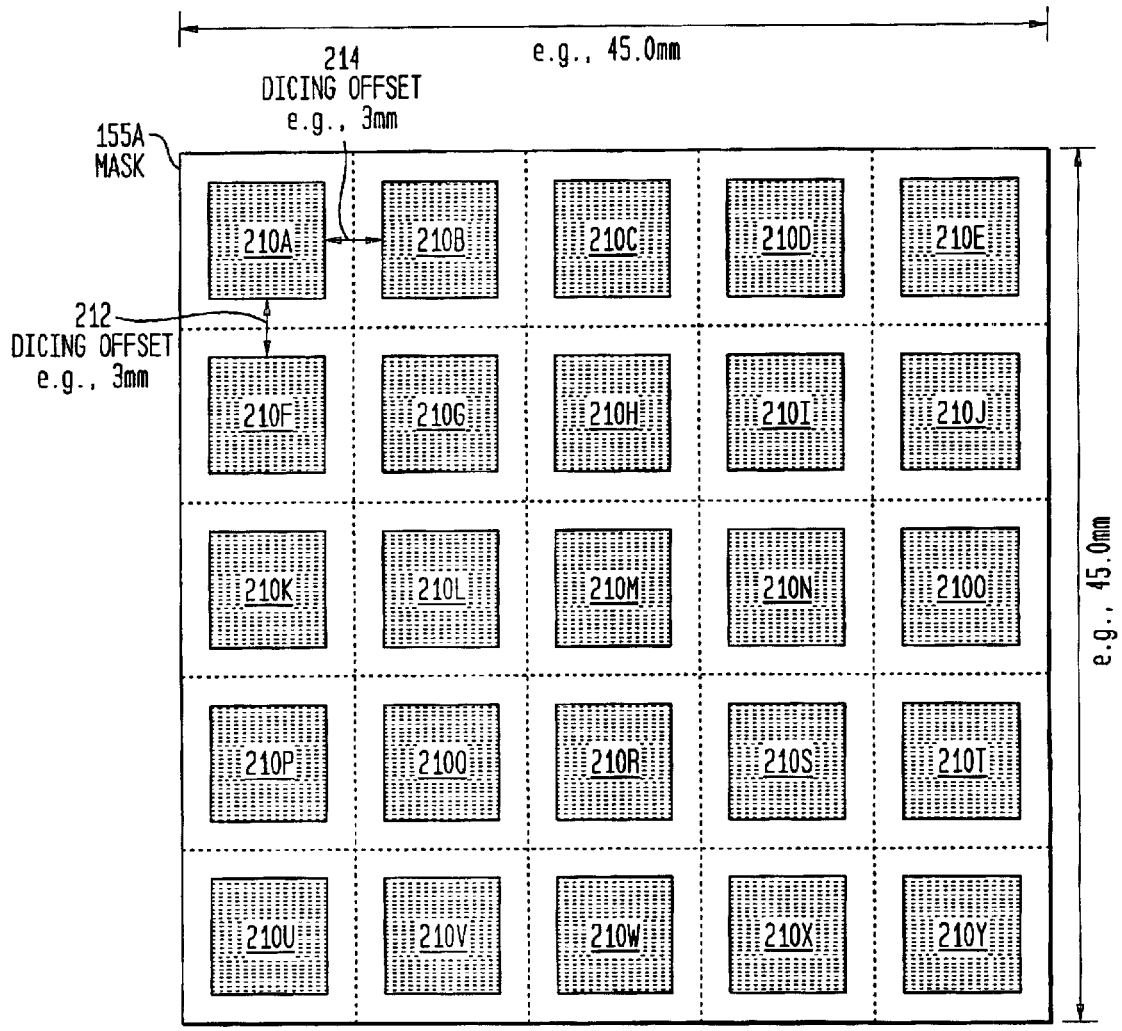

Probe Arrays Synthesized Using Masks of FIGS. 2A–B

FIGS. 2A and 2B are simplified graphical representations of a mask having a conventional arrangement of reticles for synthesizing probe arrays. FIGS. 2C through 2F are simplified graphical representations of a conventional method for synthesizing probe arrays using one or more masks of the conventional type shown in FIGS. 2A and 2B.

FIG. 2B shows mask 155A having illustrative dimensions of 45 millimeters by 45 millimeters. Mask 155A includes reticles 210A through 210Y, generally and collectively referred to hereafter as reticles 210. FIG. 2A shows representative reticle 210A having illustrative dimensions of 6 millimeters by 6 millimeters. Each of reticles 210 includes open or occluded areas for respectively specifying the coupling, or not, of a monomer in this example. As will be appreciated by those of ordinary skill in the relevant art, the selective coupling of monomers as specified by a reticle may take place on millions of locations on a substrate. For example, a reticle may specify selective coupling locations for thousands of probe sets corresponding, for example, to thousands of genes or EST's of potential interest. Moreover, each of the probe sets may include tens of probes, each of which may include many thousands of polymers having a same sequence.

As indicated in FIGS. 2A and 2B, adjacent ones of reticles 210 are surrounded by a dicing offset 212 that, in this example, is 3 millimeters. As will be described in greater detail below, dicing offset 212 is provided on the reticle so that corresponding areas of the substrate will not contain probes. The substrate is diced, i.e., cut, through the areas thus provided. It will be appreciated by those of ordinary skill in the relevant art that mask 155A is a simplified representation because, among other things, it does not show alignment features typically provided to facilitate the alignment of masks and substrates during probe synthesis. For example, a distinctive feature, such as a checkerboard pattern (not shown), may be provided in some parts of the mask occupied by dicing offsets 212 and/or by one or more of reticles 210. Alignment features may thus displace reticles in some instances so that, for example, mask 155A includes 23 reticles rather than the 25 reticles shown in this example.

In accordance with conventional techniques well known to those of ordinary skill in the relevant art, a number of masks having reticles arranged in the fashion shown in FIG. 2B may be used to synthesize probe arrays. Mask 155A-1 of FIG. 2C is one such mask having reticles designed for a first light-exposure step. Mask 155A-1 includes reticles 210A-1 to 210Y-1 (generally and collectively referred to as reticles 210-1), and dicing offsets 212. In the first light-exposure step, mask 155A-1 is aligned over wafer 240 as represented in FIG. 2D. Wafer 240 is a substrate having dimensions commensurate with the areas on which probes are to be synthesized, as determined by reticles 210, including reticles 210-1. For convenience wafer 240 is shown as having the same dimensions as mask 155A, but it need not be so. Light is directed through the reticles in order to selectively enable coupling of a monomer to areas on wafer 240. Each of reticles 210-1 determines the locations of monomer coupling in an area that will correspond to a probe array after dicing of the wafer. For example, reticle 210A-1 determines monomer coupling in a first light-exposure step in the synthesis of an area of wafer 240 that will become probe array 230A. Array 230A after the first light-exposure step is represented in FIG. 2D as area 230A-1 of wafer 240. For convenience, this and other areas may hereafter be referred to generally and collectively as probe arrays 230-1.

A second light-exposure step is represented in FIGS. 2G and 2H. As will be understood by those of ordinary skill in the relevant art, various other synthesis steps (not shown) typically are undertaken between the first and second light-exposure steps, such as washing a monomer and other reagents over wafer 240 so as to couple monomers at locations determined by reticles 210-1 and to add photochemically removable protecting groups so that the next cycle of synthesis can be initiated. Mask 155A-2 is used in this second light-exposure step, and reticles 210-2 of this second step are aligned over the same areas as were corresponding reticles 210-1 of step one in this example. A monomer is washed over wafer 240, thereby coupling them to locations now having zero, one, or two monomers, depending on whether the corresponding location in masks 155A-1 and corresponding location in masks 155A-2 were both occluded, not occluded in mask 155A-1 and occluded in mask 155A-2, or not occluded in both masks, respectively. Thus, wafer 240 includes, after this second cycle, probe array areas 230-1,2 (shown for convenience simply as "1, 2" in FIG. 2H) having probes at locations determined by reticles 210-1 of mask 155A-1 and reticles 210-2 (shown for convenience simply as "2" in FIG. 2G) of mask 155A-2.

Figure 2F:
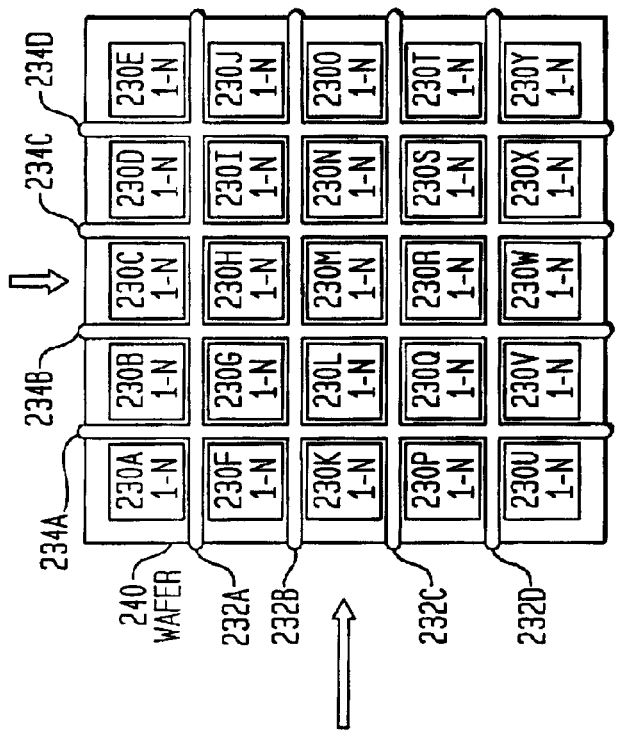
Figure 2E:
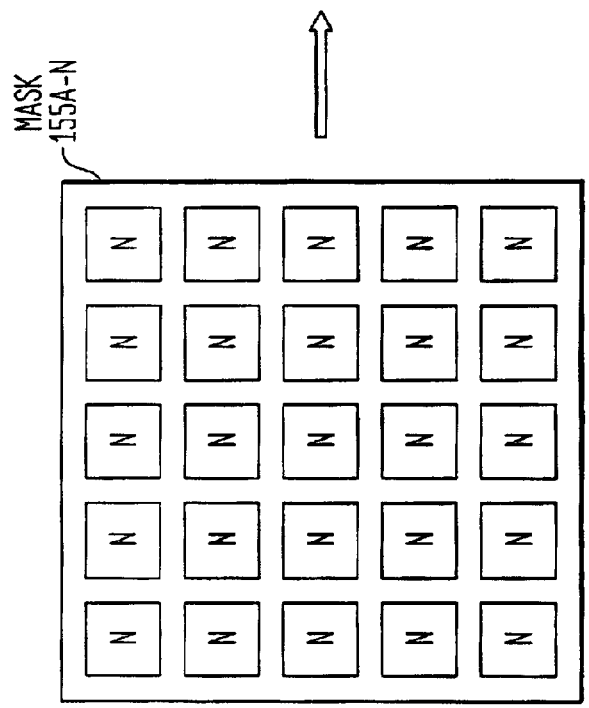

These synthesis cycles may continue using dozens of masks 155A, each of which has reticles 210 arranged in a same configuration and aligned over the same areas of wafer 240. The last of these dozens of masks is represented in FIG. 2E as mask 155A–N. FIG. 2F shows wafer 240 after the last of the synthesis cycles has been completed, at which time wafer 240 consists of probe array areas 230A–230Y, each having probes determined by reticles in corresponding positions of masks 155A-1 through 155A–N. For example, reticle 210A-1 through reticle 210A–N has sequentially been aligned with probe array area 230A(1–N) over the N cycles. In accordance with conventional techniques, wafer 240 then is diced through dicing offsets 212 as indicated by horizontal dicing lines 232A–232D (hereafter, "dicing lines 232") and vertical dicing lines 234A–234D (hereafter, "dicing lines 234"). The result is the physical separation from wafer 240 of 25 synthesized probe arrays 230.

Notably, the dicing operation in accordance with this conventional approach typically requires that a significant portion of masks 155A be set aside for dicing offsets 212. The example of 3-millimeter offset areas separating each probe array area is typical in order to accommodate the thickness of the cut made by conventional techniques. Also, the number of masks needed in accordance with the conventional approach of FIGS. 2A–2F is equal to the number of synthesis cycles, i.e., the number of times that each probe array area is exposed to light. For example, in some Affymetrix® GeneChip® arrays, 25-mer oligonucleotide probes are synthesized in 75 synthesis cycles; that is, 75 masks are used. The mask set required for synthesis of these arrays thus is relatively expensive, and the synthesis process is relatively lengthy.

Probe Arrays Synthesized Using Masks of FIGS. 3A–D and 4A–D

Figure 3B:
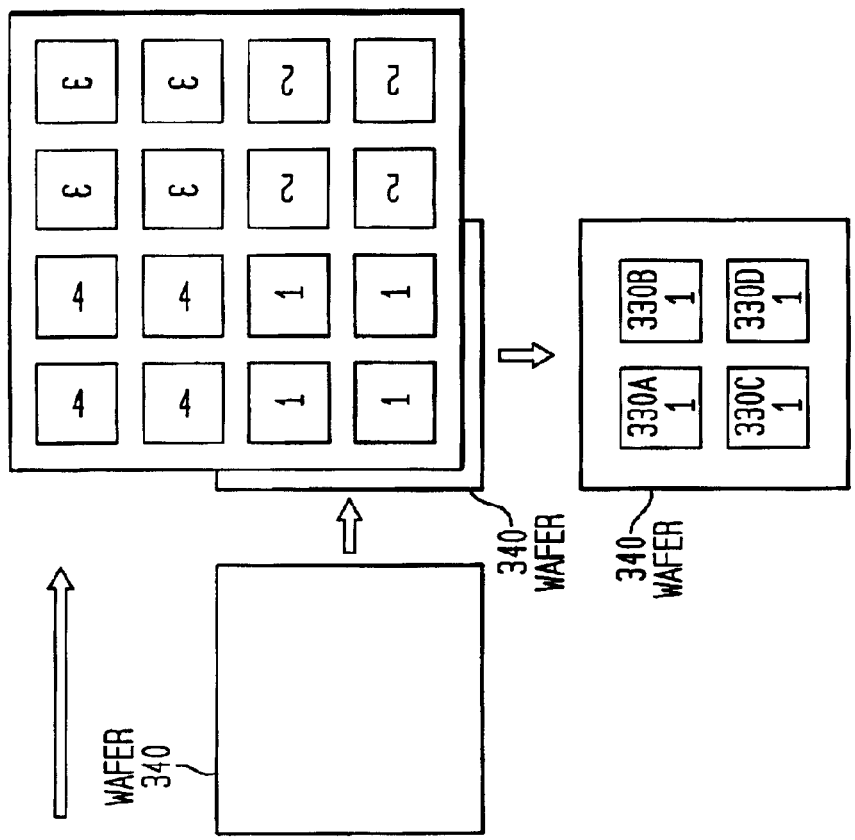
Figure 3A:
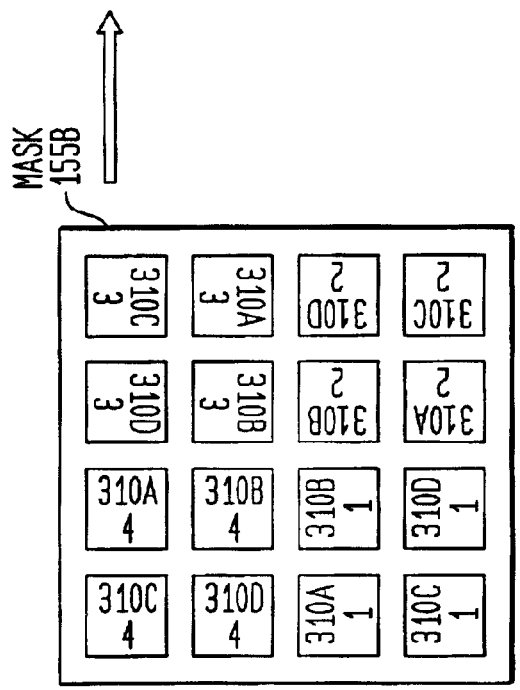

FIG. 3A is a simplified graphical representation of another mask design that provides the advantage of generally requiring a smaller mask set, although the disadvantage noted above with respect to the dedication of wafer area to dicing offsets is not alleviated. Illustrative mask 155B of FIG. 3A is made up of 16 reticles consisting of four reticles in each of four groups. Reticles 310A-1 through 310D-1 are aligned during a first light-exposure step over probe array areas of wafer 340 shown in FIG. 3C as areas 330A-1 through 330D-1. (As in the previous examples, alignment features and the details of the reticles are not shown, but their implementation in accordance with various techniques will readily be appreciated by those of ordinary skill in the relevant art.) Rather than employing a second mask for the second light-exposure step, however, mask 155B is rotated and/or translated so that the second set of four reticles, 310A-2 through 310D-2, are aligned over the same probe array areas of wafer 340. This alignment is shown in FIGS. 3C and 3D wherein reticles 310A-2 through 310D-2 (shown simply as reticles "2" for convenience) are aligned over wafer 340 having monomers synthesized in the first cycle. The result, after the second synthesis cycle is completed, is represented in FIG. 3E where wafer 340 is shown with reticle areas 330A–330D having monomers coupled to them in accordance with light-exposure steps 1 and 2. In the illustrated example, four such light-exposure steps may be undertaken using the same mask 155B. Additional masks having the same arrangement of reticles may then be used to complete the N cycles of N light-exposure steps, resulting in wafer 340 as shown in FIG. 3F. Four probe arrays may then be diced from wafer 340 by cutting along dicing lines 332 and 334.

Thus, while the number of masks used to synthesize probe arrays 330A through 330D is one-fourth the number used to synthesize probe arrays 230A through 230Y of the previous example, the number of probe arrays from the mask set is reduced from 25 to four. As is now evident, both the number of probe arrays synthesized with a mask set and the number of masks in a mask set can be altered by changing the size and/or geometry of the mask and reticles. As one of many possible examples, mask 155B could have been made with four groups of nine reticles (i.e., 36 reticles per mask for the synthesis of nine probe arrays using four light-exposure steps per mask) by increasing the size of the mask and/or reducing the size of the reticles. Similarly, the mask of this alternative example could consist of nine groups of four reticles (i.e., 36 reticles per mask for the synthesis of four probe arrays using nine light-exposure steps per mask).

Many arrangements of reticles are possible that allow multiple synthesis cycles to be accomplished using each mask. One alternative arrangement is illustrated in FIGS. 4A–E. FIG. 4A is a simplified graphical representation of a mask 155C that has six groups of two reticles each (i.e., 12 reticles per mask for the synthesis of two probe arrays using six light-exposure steps per mask). Reticles of the first group, i.e., reticles 410A-1 and 410B-1, are aligned over probe array areas 430A and 430B in a first light-exposure step, as shown in FIG. 4B. As shown in FIG. 4C, reticles 410A-2 and 410B-2 (shown for convenience simply as "2") are aligned over the same probe array area of wafer 440 in a second light-exposure step. This process is repeated for the third group, as shown in FIG. 4D, and for the remaining three of the six groups of illustrative mask 155C. If more than six synthesis cycles are used, the process is similarly repeated for additional groups in additional masks in which reticles are arranged in the configuration of mask 155C. The result is shown in FIG. 4E in which dicing line 432 is cut to separate wafer 440 into probe array 430A and probe array 430B, each synthesized using N light-exposures. As will now be evident, any number of groups, having any number of reticles each, could similarly be constructed. As one of many possible examples, mask 155C could have been arranged to have 21 groups of two reticles each (i.e., 42 reticles per mask for the synthesis of two probe arrays using 21 light-exposure steps per mask, not shown). In all of these arrangements, a dicing offset of an illustrative 3 millimeters is employed between reticles of the same group (i.e., between reticles exposed during the same light-exposure step).

Thus, in all of the preceding variations noted with respect to FIGS. 3A–F and 4A–E, the disadvantage remains that reticles are separated by dicing offsets 312 and 412. As noted, these dicing offsets are reserved for the purpose of allowing dicing of probe arrays through locations on wafers 340 and 440, respectively, as determined by the separation of reticles in the same group (i.e., reticles exposed during the same light-exposure step). The inclusion of dicing offsets 312 and 412 reduce the area of masks 155B and 155C, respectively, that can be dedicated to reticles.

Probe Arrays Synthesized Using Masks of FIGS. 5A–C, 6I, 6K, and 6L

Figure 5A:
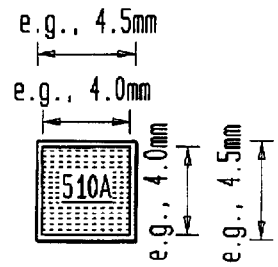
FIG. 5C is a simplified graphical representations of one embodiment of a mask having substantially contiguous reticle areas (a representative of which is shown in greater detail in FIG. 5B) made up of substantially contiguous reticles (a representative of which is shown in greater detail in FIG. 5A)
Figure 5B:
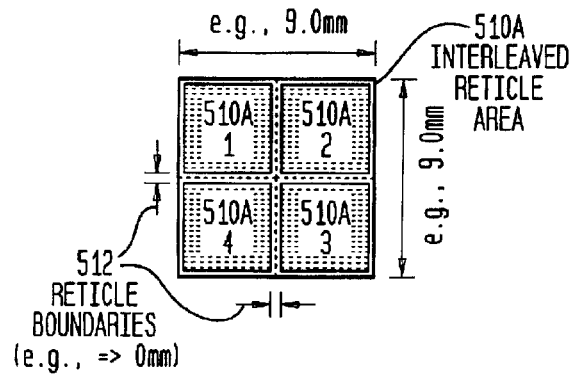
Figure 5C:
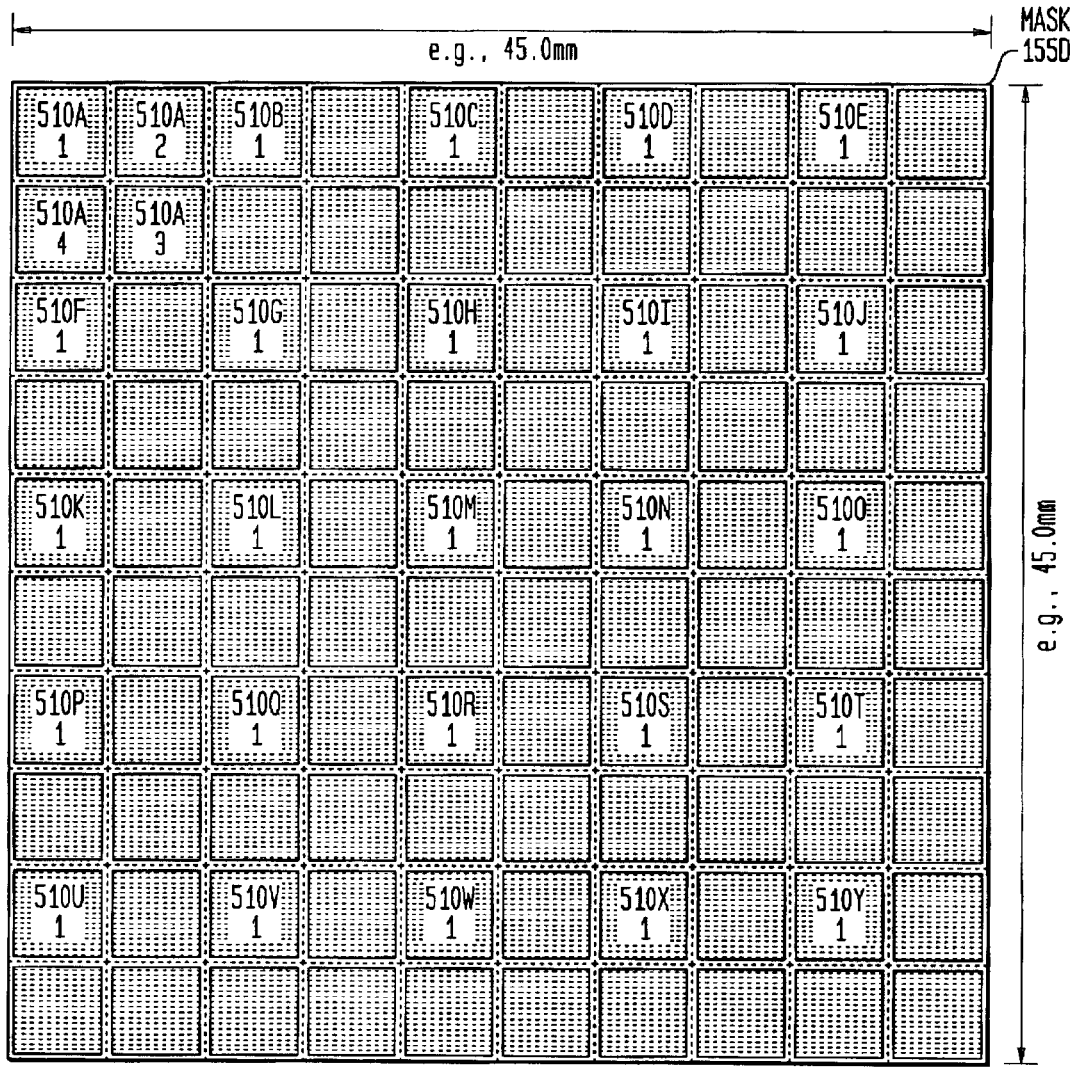

A number of advantages, as compared for instance to the previous mask examples, can be attained by employing a mask design such as that now described in relation to FIGS. 5A–C, 6I, 6K, and 6L. For convenience, and for reasons that will be described below, this advantageous design may sometimes be referred to hereafter as the "interleaved" design, and masks having this design are sometimes referred to as "interleaved" masks. Significantly, the interleaved design need not reserve areas of the mask so that those reserved areas will provide, by themselves, an area on a wafer through which dicing cuts may be made. Rather, as shown in FIG. 5C, reticles in many implementations of interleaved masks may be spaced as closely together as desired without regard to reserving space on the substrate for dicing. In some implementations in which reticles are less wide than the width needed to make a dicing cut, a small boundary area may be provided so that cuts may be made through the boundary area together with discard areas. Notably, the small boundary areas of these implementations are supplemented by the discard areas to provide for dicing, as contrasted with the dicing offsets of previous examples that themselves were sufficiently wide to provide an area for a dicing cut.

Interleaved mask 155D of FIG. 5C is assumed for illustrative and comparative purposes to be 45 millimeters by 45 millimeters, the same dimensions illustratively assumed for conventional mask 155A of FIG. 2B. Whereas the reticles of conventional mask 155A are separated from each other by 3 millimeter dicing offsets, the reticles of interleaved mask 155D are substantially contiguous on the mask. As shown in FIG. 5A, the reticles of interleaved mask 155D are smaller than those of conventional mask 155A; e.g., they are illustratively assumed to be 4.0 millimeters by 4.0 millimeters. One hundred reticles (generally and collectively referred to as reticles 510) may thus be placed on mask 155D (as compared to 25 larger reticles, with dicing offsets on mask 155A). In the illustrated implementation, reticles 510 are separated from each other by a small boundary that is 0.5 millimeters wide. In other implementations, this boundary could be arbitrarily small, including implementations in which there are no boundaries between reticles; i.e., they abut each other.

There are a variety of practical reasons, not related to providing discard areas on a wafer, for optionally providing boundaries of non-zero width. One reason for providing nonzero-width boundaries is related to the process of scanning probe arrays. As shown in FIG. 5B, reticles on an interleaved mask may be described as being arranged in groups referred to herein as "interleaved reticle areas." For example, in FIG. 5B, reticles 510A-1, 510A-2, 510A-3, and 510A-4 constitute an interleaved reticle area 510A. Each of the reticles in interleaved reticle area 510A is associated with a same synthesis area on a wafer, referred to for illustration of this example as the first synthesis area. Reticle 510A-1 is aligned with the first synthesis area during a first light-exposure step, reticle 510A-2 is aligned with the same first synthesis area during a second light-exposure step, and so on. As described in greater detail below in relation to FIGS. 6D through 6H, light shown through reticles 510A-2, 510A-3, and 510A-4 (i.e., the "out-of-step" reticles for the first cycle) during the first light-exposure step typically will result in the coupling of a monomer used during the first synthesis cycle on areas of the substrate surrounding the first synthesis area. Similarly, light shown through reticles 510A-1, 510A-3, and 510A-4 (the "out-of-step" reticles for the second cycle) during the second light-exposure step typically will result in the coupling of a monomer used during the second synthesis cycle on areas of the substrate surrounding the first synthesis area, and so on for the third and fourth cycles. However, as described in greater detail below, the resulting polymers that may be coupled to the substrate surrounding the first synthesis area by out-of-step reticles generally are not related to any intended probe sequence and, in any event, typically are not used, or intended to be used, as probes. Thus, the area surrounding the first synthesis area that may contain polymers synthesized by alignment of out-of-step reticles may be referred to for convenience as "discard areas." Even though polymers in discard areas located along the boundaries with the first synthesis area are not synthesized for the purpose of hybridizing with potential targets, hybridize may occur.

When irradiated by a scanner, any labeled targets that have hybridized with polymers in discard areas around the first synthesis area will provide detectable excitation radiation. This excitation radiation may interfere with the identification of intended probes within the first synthesis area. For example, a human operator or a software algorithm attempting to identify corners of the probe array created from the first synthesized area may be confused by emissions detected from labeled targets that happened to hybridize with the polymer in discard areas near the corners. Identification of corners of a probe array is a typical method for imposing an "alignment grid" to help in identifying probes from scanned images, as described in greater detail in U.S. Pat. No. 6,090,555 to Fiekowsky, et al., which is hereby incorporated by reference herein in its entirety for all purposes. By providing a small boundary between reticles, a small separation is provided between a synthesis area and its surrounding discard areas, and thus the likelihood of confusion may be reduced. However, providing a non-zero boundary for this reason is optional and need not be implemented in various implementations.

Another reason for optionally providing boundaries of non-zero width is that the design of the machinery used to handle, align, and/or synthesize masks and/or wafers may make it convenient to employ masks and/or wafers of particular outside dimensions. For instance, a mask or wafer having the 45 millimeter by 45 millimeter dimensions of the present example may be more convenient than one of 40 millimeters on a side. Thus, whereas 100 reticles of 4 millimeters by 4 millimeters each could fit on a square mask of 40 millimeters on a side and such an implementation is optional, this arrangement of abutting reticles would merely leave empty space on the edges of a square mask or wafer having 45 millimeters on a side. Thus, a separation of 0.5 millimeters may be provided between reticles of this size on a square mask of 45 millimeters on a side without affecting the efficiency of mask usage. It may be advantageous in some cases to increase the size of each reticle from 4.0 to 4.5 millimeters on a side, thus allowing the synthesis of additional probes using abutting reticles. However, it also is possible that the smaller reticle size is sufficient for synthesis of the desired number of probes, and there thus may be no reason to increase the reticle size. Also, the equipment used for packaging, handling, or processing (e.g., hybridizing, washing, scanning) probe arrays may make it convenient to have probe arrays of a particular size. Thus, while larger reticles and thus larger probe arrays might be possible for masks or wafers of a particular size, there may be no reason to use the larger reticles.

Yet another practical reason that boundaries of non-zero width may be employed is if the width of a discard area is less than the minimum width needed for dicing, and each synthesis area is separated from its neighboring synthesis areas by no more than one discard area. For example, if each reticle is a square having sides of 2.53 millimeters, and the interleaved reticle areas have four reticles that abut each other, then the discard areas around each synthesis area on a wafer will be 2.53 millimeters. For implementations in which the area reserved for the dicing cut must be no less than 3 millimeters wide, then an addition of 0.5 millimeters increases the effective size of the discard area to provide the extra margin for dicing.

Figure 6A:
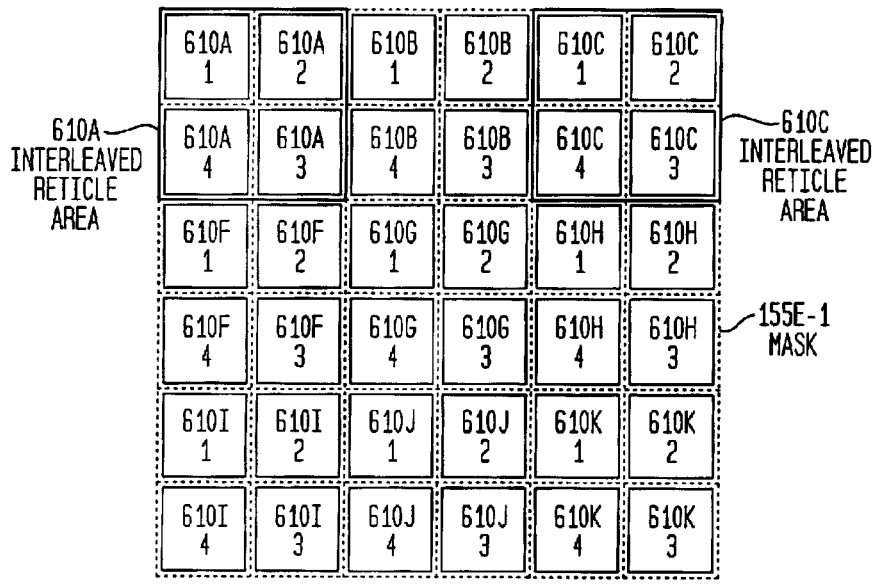
FIGS. 6A through 6C are simplified graphical representations of another embodiment of a mask having substantially contiguous reticles and reticle areas.
Figure 6B:
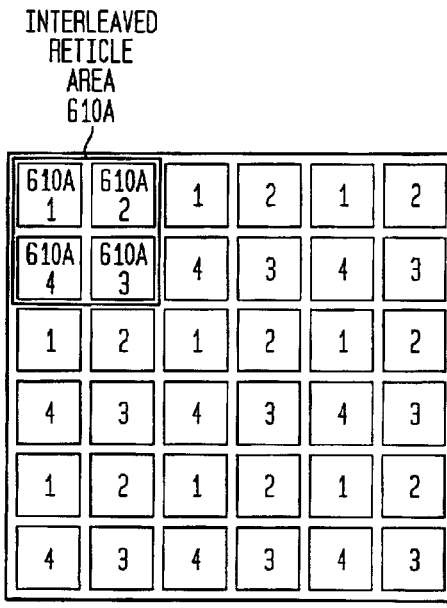
Figure 6C:
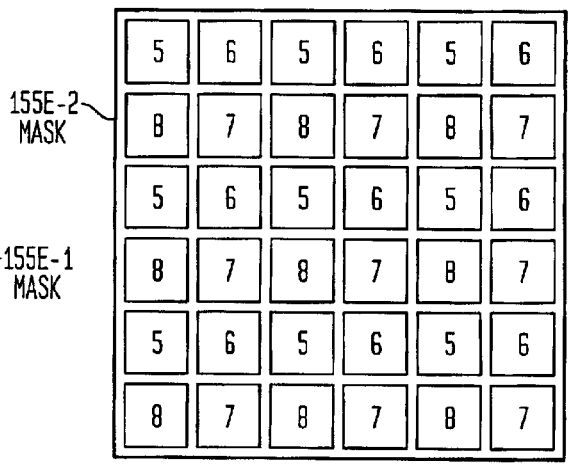

The use of interleaved masks to synthesize polymers on a substrate is now further described in relation to FIGS. 6A through 6M. FIG. 6A is a graphical representation of an interleaved mask 155E-1 similar to mask 155D of FIG. 5C except that fewer reticles are included for ease of illustration. Mask 155E-1 is one of a set of masks 155E that maybe used in accordance with this example. Mask 155E-1 has 36 reticles grouped together in interleaved reticle areas having four reticles each. It will be understood that these are merely illustrative numbers both with respect to the number of reticles in the mask and the number of reticles in an interleaved reticle area. The four reticles in interleaved reticle area 610A are labeled 610A-1 through 610A-4, the four reticles in interleaved reticle area 610B are labeled 610B-1 through 610B-4, and so on for interleaved reticle areas 610C through 610K (all of which are generally and collectively referred to as interleaved reticle areas 610). Reticles 610A-1, 610B-1, and so on through 610K-1, are aligned with a synthesis area during a first light-exposure step. Similarly, reticles 610A-2, 610B-2, and so on through 610K-2, are aligned with a synthesis area during a second light-exposure step, and so on for all four steps for which mask 155E-1 is used. For ease of illustration, this nomenclature is shown in simplified form in FIG. 6B and subsequent figures, wherein only the step numbers are shown and the interleaved reticle areas are not explicitly labeled. FIG. 6C shows a second mask of the set, interleaved mask 155E-2, having the same configuration as mask 155E-1 but used for synthesis of polymers during light exposure steps 5 through 8.

FIG. 6D shows interleaved mask 155E-1 aligned with wafer 600 for a first synthesis cycle. Wafer 600 is shown as being slightly smaller than mask 155E-1, but this difference is provided for ease of illustration only. Wafer 600 may also be the same size, or larger than, masks 155E. In FIG. 6D, first-step reticles in each interleaved reticle area (i.e., reticles 610A-1, 610B-1, and so on through 610K-1) of mask 155E-1 are aligned with synthesis areas. Synthesis areas are highlighted for illustrative purposes by dark lines. During the first synthesis cycle, light is shown through the first-step reticles to de-protect linker molecules on wafer 600 as determined by the non-occluded portions of each first-step reticle. Light may (but need not) also be shown during this first light-exposure step through all the other reticles of mask 155E-1, but any polymers thus synthesized are in discard areas of wafer 600.

FIG. 6E shows interleaved mask 155E-1 aligned with wafer 600 for a second synthesis cycle. Either wafer 600, mask 155E-1, or both may be moved to accomplish this alignment, and/or optical elements may be used to accomplish the alignment without necessarily moving either wafer 600 or mask 155E-1. In FIG. 6E, second-step reticles in each interleaved reticle area (i.e., reticles 610A-2, 610B-2, and so on through 610K-2) of mask 155E-1 are aligned with synthesis areas. Reticle 610A-2 is aligned with the same synthesis area with which reticle 610A-1 was aligned during the first synthesis cycle, reticle 610B-2 is aligned with the same synthesis area with which reticle 610B-1 was aligned during the first synthesis cycle, and so on for each interleaved reticle area. That is, each reticle of a same interleaved reticle area is aligned with a particular synthesis area common to the reticles of that interleaved reticle area during the cycle in which that reticle is used for synthesis of probes. Typically, out-of-step reticles (i.e., those not used during a particular cycle for synthesis of probes and thus not aligned with a synthesis area) are aligned with discard areas.

FIGS. 6F and 6G show interleaved mask 155E-1 aligned with wafer 600 for third and fourth synthesis cycles, respectively. In similar fashion, mask 155E-2, and other masks that may be included in mask set 155E, are sequentially aligned and then re-aligned over synthesis areas.

FIG. 6H shows wafer 600 after N synthesis cycles, where each mask of mask set 155E had been used for four cycles and then replaced with the next in the set. As shown in FIG. 6H, wafer 600 includes synthesis areas 630A through 630I (generally and collectively referred to as synthesis areas 630). Dicing lines 612 and 614 may be cut so as to physically separate wafer 600 into nine substrates suitable for packaging or otherwise to be used as probe arrays. It will be understood that the number, orientation, and placement of dicing lines 612 and 614 in FIG. 6H are illustrative only. For example, if it is desired to dice wafer 600 so that the area of the separated substrates are as close as possible to that of the synthesis area, then the dicing lines could be shifted closer to the synthesis areas and additional dicing lines added as necessary.

FIGS. 6I and 6J provide further detail regarding the dicing of wafer 600 after the N light-exposure steps have been completed. FIG. 6I shows the upper left portion of wafer 600 consisting of synthesis area 630A after N light-exposure steps, surrounded by discard areas 632A, 634A, and 636A. This region of a wafer consisting of a synthesis area surrounded by discard areas may sometimes be referred to herein as a single-chip interleaved area, such as area 640 of the example of FIG. 6I. The term "single-chip" is used to indicate that dicing lines may be cut, in any manner, through the discard areas surrounding the synthesis area in order to provide a separate probe array (e.g., a separate GeneChip® probe array). As can be seen from FIG. 6D, reticles 610A-2, 610A-3, and 610A-4 are aligned with discard areas 632A, 634A, and 636A, respectively, during light-exposure step one. FIG. 6E shows that, during light-exposure step two, reticle 610A-3 is aligned with discard area 636A, reticle 610B-1 is aligned with discard area 632A, and reticle 610B-4 is aligned with discard area 634A. FIGS. 6F and 6G similarly show the alignment of reticles with both synthesis areas and discard areas during light-exposure steps three and four, respectively. FIG. 6J shows how dicing lines 612 and 614 may pass through discard areas so that synthesis areas 630 may be diced to provide physically separate probe arrays.

FIGS. 6K through 6M show an implementation of the interleaved mask design using another arrangement of reticles in interleaved reticle areas. In this example, each interleaved reticle area, such as area 645A of FIG. 6K, includes six reticles arranged in two rows and three columns. Thus, for example, reticles 647A-1 through 647A-6 may be sequentially aligned over synthesis area 650A of single-chip interleaved area 660 of wafer 670 (shown in FIGS. 6L and 6M) during light-exposure steps one through six, respectively. In the manner described above, discard areas 652A, 654A, 656A, 658A, and 659A are formed around synthesis area 650A during these, and other, light exposure steps. The resulting synthesis areas 650A through 650I are shown after N light-exposure steps in FIG. 6M, surrounded by discard areas through which cuts may be made, for example, along dicing lines 662 and 664.

It will be understood that the examples of FIGS. 5A through 5C, and 6A through 6M, are illustrative only, and that many combinations of numbers of rows and columns of reticles in interleaved reticle areas may be used in alternative implementations. Moreover, patterns other than rows and columns may also be employed to constitute interleaved reticle areas. Also, it is not required that reticles be square, as shown for convenience in these figures. They may be any other shape.

As will now be appreciated, a significant advantage of using interleaved masks is that the number of masks in a mask set generally may be substantially reduced as compared to designs in which portions of the mask are dedicated to dicing offsets. At the same time, the productivity of interleaved masks generally need not be compromised in terms of the number of probe arrays synthesized. These advantages are demonstrated, for example, by comparing conventional mask 155A of FIG. 2B with interleaved mask 155D of FIG. 5C. The size of each mask has illustratively been assumed to be the same: 45 millimeters on a side. As noted, details such as the use of alignment features are not considered with respect to either mask for sake of clarity and ease of illustration. The number of probe arrays synthesized from a single mask set is also the same for each of the masks: 25 synthesis areas yielding 25 probe arrays. It is now assumed that the probe arrays are synthesized using N light-exposure steps. Employing the conventional design of mask 155A, N masks are therefore used. Employing the interleaved design of mask 155D, N/4 masks (or N/4 rounded down to an integer, plus 1, if N is not evenly divisible by 4) are used. As noted, the savings in terms both of time and expense typically are therefore significant. Moreover, these savings can be driven further by employing interleaved designs in which additional steps are implemented by reticles of the same mask, as in mask 155F of FIG. 6K in which six light-exposure steps are implemented using each mask.

As is evident, increasing the number of light-exposure steps implemented on each mask, assuming the mask size remains the same, generally is accomplished by reducing the size of the reticles. Smaller reticles generally results in smaller synthesis areas, which generally means, assuming a constant probe density, that fewer probes may be synthesized on each synthesis area and thus fewer probes are included in the resulting probe arrays. However, this effect is ameliorated by at least two considerations. First, the mask area is efficiently used in accordance with the interleaved design because little or no space need be provided between reticles. Thus, more information can generally be carried by an interleaved mask than by conventional masks in which dicing offsets, generally carrying no information, are included.

Second, there are important applications in which the savings in time and money achieved by using interleaved masks far outweighs any reduction in the number of probes in the resulting probe arrays. For example, there is considerable demand among users for custom-made arrays that can be provided relatively quickly and inexpensively. A user of custom-made arrays may not require that tens of thousands of genes or EST's be probed in a single array. Rather, the user may require probe arrays representing far fewer sequences, e.g., 100 to 1,000 genes or EST's. Moreover, the user may not need large numbers of the customized arrays. For example, a dozen arrays may be sufficient. For user demand of this type, the previous example of a reticle of 2.53 millimeters on a side generally provides sufficient probe density using conventional probe synthesis technology while producing sufficient number of probe arrays using far fewer masks as compared to conventional mask designs. For example, if the boundary area between reticles has a width of 0.47 millimeters (so that the boundary area plus discard area is sufficient for a 3 millimeter dicing cut), then the illustrative square mask of 45 millimeters on a side can accommodate 15×15=225 reticles. If these 225 reticles are applied to 15 light-exposure steps, then a mask set generally produces 15 square synthesis areas of 2.53 millimeters on a side and 15 probe arrays of this size. It is illustratively assumed that 75 light-exposure steps are used for complete synthesis of probes (e.g., 25-mer oligonucleotides). Thus, only five interleaved masks (75 divided by 15) are required in the illustrative mask set. Using the conventional approach represented by mask 155A, 75 masks would be needed. The fifteen-fold reduction in the size of the mask set achieved using the interleaved masks provides significant savings in time and cost while satisfying user demand with respect to probe density and number of probe arrays supplied.

Figure 7:
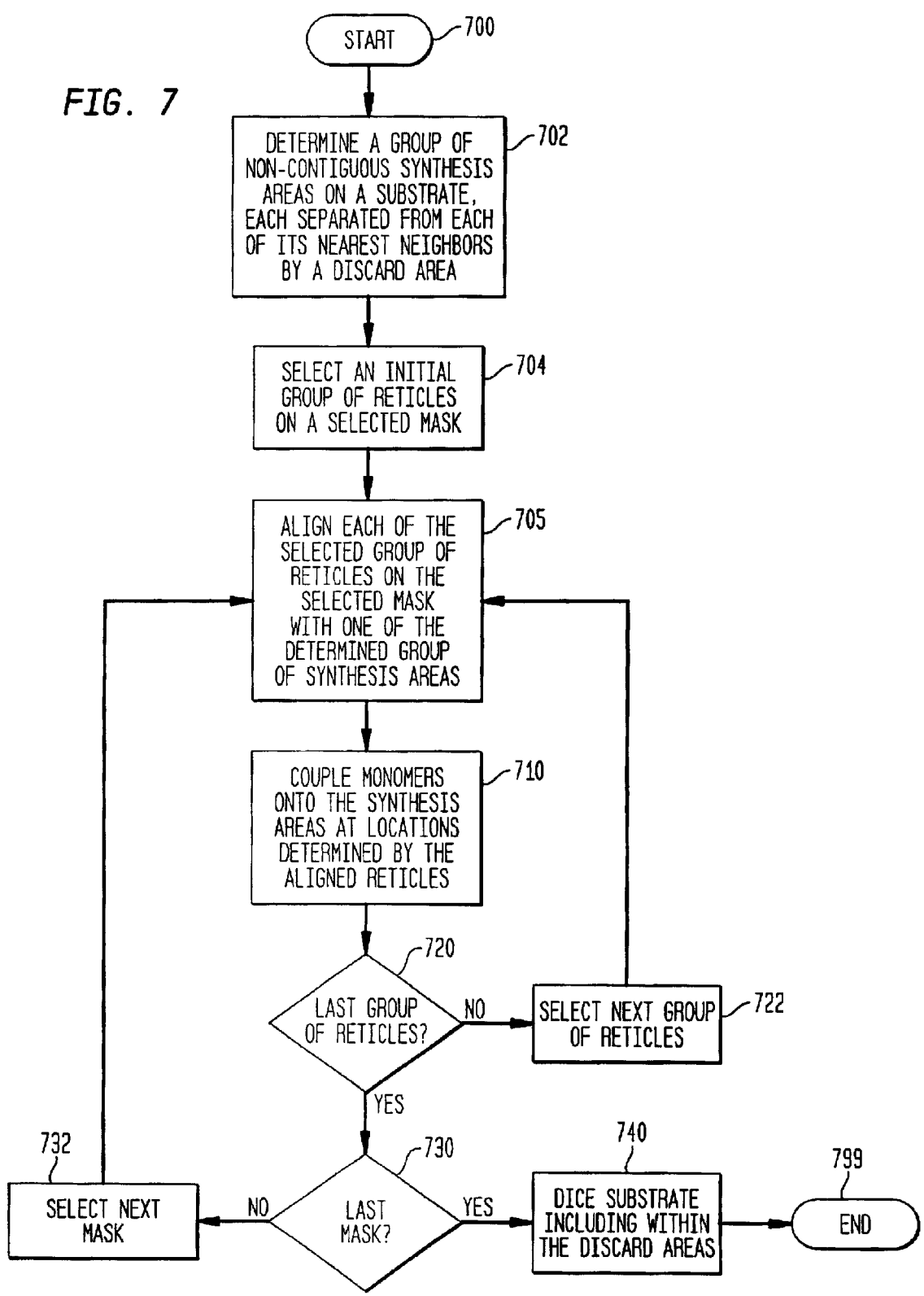
FIG. 7 is a flow diagram of one embodiment of a method for synthesizing probes on a substrate, and then dicing the substrate to provide probe arrays, using one or more masks having substantially contiguous reticles and reticle areas.

FIG. 7 is a simplified flow chart showing illustrative steps that may be employed to implement the use of interleaved masks as described above. It will be understood that many variations to these steps are possible, and that the steps may be alternatively characterized. For example, step 702 is to determine a group of non-contiguous synthesis areas on a substrate, each separated from each of its nearest neighbors by a discard area. Aspects of this step could alternatively be characterized as providing a mask having substantially contiguous interleaved reticle areas, each consisting of substantially contiguous reticles that may sequentially be aligned over a same synthesis area on a substrate. Step 704 is to select an initial group of reticles on a selected mask. For example, all first-step reticles in each of the reticle areas of a first mask could be selected. Step 705 is to align each of the selected group of reticles with one of the determined group of synthesis areas. Thus, in this example, the first-step reticles are each aligned with a synthesis area. Step 710 is to couple monomers onto the synthesis areas at locations determined by the aligned reticles. For example, monomers are coupled to locations on the synthesis areas determined by non-occluded portions of the first-step reticles, i.e., those portions through which light shown during the first light-exposure step so as to de-protect molecules on the substrate. As indicated by decision elements 720 and 730, and steps 732 and 722, this process is repeated for all of the reticles in the interleaved reticle areas for each of the masks in the mask set (i.e., for step 2 through step N reticles). Then, as indicated in step 740, the substrate may be diced through areas including discard areas to provide physically separated substrates suitable for further processing and packaging as probe arrays.

The foregoing steps, and others that may be used in numerous variations of the interleaved mask design, may be implemented, for example, in the form of computer instructions and data such as represented by desired mask characteristics 106 of FIG. 1. As described above, mask design system 101 employs mask design application 199 to operate on characteristics 106 and probe information 107 to provide mask specification files 112 and probe specification files 114. Mask manufacturing system 150 uses mask specification files 112 to produce masks 155. FIG. 8 is a simplified functional block diagram of a probe array synthesis system 800 suitable for producing synthesized probe arrays 810 based on files 112 and 114, masks 155, and various other materials (e.g., reagents 804, substrates, packaging, and other materials 806) well known to those of ordinary skill in the relevant arts.

System 800 includes a computer or controller 810, which may be any type of general purpose computer, as described above with respect to computer 100, or a dedicated processor or controller. System 800 also includes aligner 820 that, typically under the control of computer or controller 810, performs the sequential alignments of masks and substrates as specified, for example, by aspects of mask specification files 112. Thus, alignment steps of FIG. 7, or other steps for implementing an interleaved mask design, are provided to system 800 as data and/or instructions in files 112 and implemented by masks 155 produced in accordance with mask characteristics 106 embodying interleaved mask designs. A further element of system 800 is synthesizer 830 that also typically operates under the control of computer or controller 810. In accordance with techniques well known to those of ordinary skill in the art, synthesizer applies reagents 804 and materials 806 to form polymers on a substrate, and to dice the substrate, all as described above.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments. For example, some or all of the functions described as being carried out by computer or controller 810 could be carried out by aligner 820 and/or synthesizer 830.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so on, may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server or other computer. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. A method for synthesizing polymers on a substrate using at least one mask comprising:
   (a) aligning a reticle of each of a plurality of reticle areas arranged on a mask with a synthesis area on the substrate associated with each reticle area, wherein each reticle area comprises a plurality of reticles and each synthesis area is separated from its nearest neighbors by a discard area;
   (b) coupling monomers on the substrate at a plurality of locations determined by each aligned reticle; and
   (c) sequentially repeating steps (a) and (b) for at least two of the plurality of reticles of each reticle area thereby enabling formation of polymers in each synthesis area on the substrate from each of the sequentially coupled monomers;
   wherein the plurality of reticle areas are substantially contiguously arranged on the mask, and the plurality of reticles within each of the reticle areas are substantially contiguously arranged within the reticle area.

2. The method of claim 1, wherein:
   the plurality of reticles in each reticle area are arranged in a same pattern.

3. The method of claim 2, wherein:
   the pattern comprises rows and columns of reticles.

4. The method of claim 2, wherein:
   each of the plurality of reticles in each reticle area has approximately a same height H and has approximately a same width W; and
   step (a) comprises aligning by translating the at least one mask with respect to the substrate, wherein the translation distance is determined by the height H or the width W.

5. The method of claim 4, wherein:
   the translating is done by moving the substrate while the mask remains stationary.

6. The method of claim 1, wherein:
   the monomers are selected from the group consisting of nucleotides, amino acids or saccharides.

7. The method of claim 1, wherein:
   step (b) further comprises coupling a same monomer for each of the aligned reticles.

8. The method of claim 1, wherein:
   step (b) further comprises directing light through the aligned reticles to de-protect the locations for coupling.

9. A system for synthesizing polymers on a substrate using at least one mask, comprising:
   an aligner to align a reticle of each of a plurality of reticle areas arranged on a mask with a synthesis area on the substrate associated with each reticle area, wherein each reticle area comprises a plurality of reticles and each synthesis area is separated from its nearest neighbors by a discard area; and
   a synthesizer that causes monomers to be coupled on the substrate at a plurality of locations determined by each aligned reticle;
   wherein the aligner sequentially aligns at least two of the plurality of reticles of each reticle area to enable formation of polymers in each synthesis area on the substrate from each of the monomers sequentially coupled by the synthesizer; and further wherein the plurality of reticle areas are substantially contiguously arranged on the mask, and the plurality of reticles within each of the reticle areas are substantially contiguously arranged within the reticle area.

10. The system of claim 9, wherein:
    the plurality of reticles in each reticle area are arranged in a same pattern.

11. The system of claim 10, wherein:
    the pattern comprises rows and columns of reticles.

12. The system of claim 10, wherein:
    each of the plurality of reticles in each reticle area has approximately a same height H and has approximately a same width W; and
    the aligner aligns by translating the at least one mask with respect to the substrate, wherein the translation distance is determined by the height H or the width W.

13. The system of claim 12, wherein:
    the translating is done by moving the substrate while the mask remains stationary.

14. The system of claim 9, wherein:
    the monomers are selected from the group consisting of nucleotides, amino acids or saccharides.

15. The system of claim 9, wherein:
    the synthesizer couples a same monomer for each of the aligned reticles.

16. The system of claim 9, wherein:
    the synthesizer directs light through the aligned reticles to de-protect the locations for coupling.

17. A computer program product for synthesizing polymers on a substrate using at least one mask, the product comprising:
    a computer usable medium storing control logic that, when executed on a computer system, performs a method comprising:
    (a) aligning a reticle of each of a plurality of reticle areas arranged on a mask with a synthesis area on the substrate associated with each reticle area, wherein each reticle area comprises a plurality of reticles and each synthesis area is separated from its nearest neighbors by a discard area;
    (b) coupling monomers on the substrate at a plurality of locations determined by each aligned reticle; and
    (c) sequentially repeating steps (a) and (b) for at least two of the plurality of reticles of each reticle area thereby enabling formation of polymers in each synthesis area on the substrate from each of the sequentially coupled monomers;
    wherein the plurality of reticle areas are substantially contiguously arranged on the mask, and the plurality of reticles within each of the reticle areas are substantially contiguously arranged within the reticle area.

18. The product of claim 17, wherein:
    the monomers are selected from the group consisting of nucleotides, amino acids or saccharides.

* * * * *